United States Patent

Hagen et al.

[11] Patent Number: 5,561,100
[45] Date of Patent: Oct. 1, 1996

[54] PYRIDO-FUSED 4-OXO-4H-BENZOPYRANS, THEIR PREPARATION AND THEIR USE AS ANTIDOTES

[75] Inventors: Helmut Hagen, Frankenthal; Gerhard Nilz, Dannstadt-Schauernheim; Helmut Walter, Obrigheim; Andreas Landes, Limburgerhof, all of Germany

[73] Assignee: BASF Aktiengesellschaft, Ludwigshafen, Germany

[21] Appl. No.: 292,861

[22] Filed: Aug. 19, 1994

Related U.S. Application Data

[62] Division of Ser. No. 70,387, filed as PCT/EP91/02267 Nov. 29, 1991, abandoned.

[30] Foreign Application Priority Data

Dec. 8, 1990 [DE] Germany .................. 40 39 272.4

[51] Int. Cl.$^6$ .................................................. A01N 43/42
[52] U.S. Cl. .................... 504/130; 504/244; 504/289; 504/294; 504/245
[58] Field of Search .................. 548/89, 92; 549/13; 504/245, 244, 288, 130, 140

[56] References Cited

U.S. PATENT DOCUMENTS 4,255,576  3/1981  Nohara et al. ................. 546/92
5,059,240  10/1991  Hagen et al. ................. 71/94

OTHER PUBLICATIONS

Nohara et al., J. Med Chem., 28, 559–568.
Ishigura et al., Heterocycles, vol. 16, No. %, 733–740.

*Primary Examiner*—Shailendra Kumar
*Attorney, Agent, or Firm*—Keil & Weinkauf

[57] ABSTRACT

Pyrido-fused 4-oxo-4H-benzopyrans I

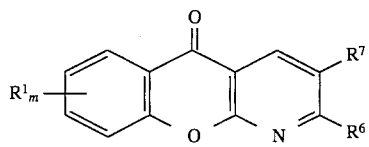

($m=0$, 1 or 2; $R^1$, $R^6$ and $R^7$ have the meanings stated in the description) and the salts of I, and herbicides which contain 2-(4-hetaryloxy)- and 2-(4-aryloxy)-phenoxyacetic acid derivatives or cyclohexenone derivatives as herbicidal active ingredients and pyrido-fused 4-oxo-4H-benzopyrans I' as antidotes.

8 Claims, No Drawings

PYRIDO-FUSED 4-OXO-4H-BENZOPYRANS, THEIR PREPARATION AND THEIR USE AS ANTIDOTES

This is a divisional of application Ser. No. 08/070,387, filed Jun. 7, 1993 now abandoned, which is a 371 of PCT/EP91/02267, filed Nov. 29, 1991.

The present invention relates to pyrido-fused 4-oxo-4H-benzopyrans of the general formula I

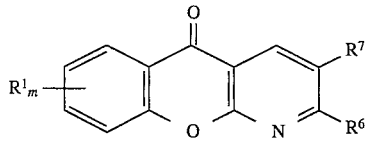

where m is 0, 1 or 2, and the radicals $R^1$ may be different when m is 2, $R^1$ is hydrogen, hydroxyl, halogen, nitro, $C_1$–$C_6$-alkyl, $C_1$–$C_6$-alkoxy, $C_1$–$C_6$-haloalkyl, $C_1$–$C_4$-haloalkoxy, $C_1$–$C_4$-alkylthio or a group $NR^2R^3$, $R^2$ is hydrogen or $C_1$–$C_4$-alkyl, $R^3$ is hydrogen, $C_1$–$C_4$-alkyl or a group —CO—$R^4$, —CS—$R^4$ or —$SO_2$—$R^5$, $R^4$ is $C_1$–$C_{20}$-alkyl, $C_1$–$C_6$-haloalkyl, $C_3$–$C_8$-cycloalkyl, $C_1$–$C_3$-aralkyl, amino, $C_1$–$C_4$-alkylamino, di-$C_1$–$C_4$-alkylamino, or phenyl or phenylamino where the aromatic ring may carry from one to three of the groups stated for $R^1$, $R^5$ is $C_1$–$C_4$-alkyl or is phenyl which may carry from one to three of the groups stated for $R^1$, $R^6$ is hydroxyl, $C_1$–$C_6$-alkoxy, $C_1$–$C_6$-alkyl or a group —NH—$R^8$ or —N($C_1$–$C_4$-alkyl)—$R^8$ where $R^8$ has one of the meanings of $R^3$, or $R^6$ is phenyl which may carry from one to three of the groups stated for $R^1$, or is $C_1$–$C_4$-alkyl-substituted 4-methyl-5-oxoimidazolin-2-yl or a group —CO—$R^9$ or —CS—$R^9$, $R^7$ is cyano or $C_1$–$C_6$-alkyl or is phenyl which may carry from one to three of the groups stated for $R^1$, or is a group —CH=N—$R^{10}$, —C($C_1$–$C_4$-alkyl)=N—$R^{10}$, —CO—$R^{11}$ or —CS—$R^{11}$, $R^9$ and $R^{11}$ are each $C_1$–$C_6$-alkyl, $C_1$–$C_6$-alkoxy, hydroxyl, amino or $C_1$–$C_4$-alkylamino or is branched $C_2$–$C_6$-alkyl which is substituted by an amido group $CONH_2$, or is di-$C_1$–$C_4$-alkylamino or aminophenyl where the aromatic ring may carry from one to three of the groups stated for $R^1$, $R^{10}$ is $C_1$–$C_4$-alkyl or $C_3$–$C_8$-cycloalkyl or is phenyl which may carry from one to three of the groups stated for $R^1$, or is hydroxyl, $C_1$–$C_8$-alkoxy or a group —O—CO—$R^{12}$ or —O—CS—$R^{12}$ where $R^{12}$ is $C_1$–$C_{20}$-alkyl, $C_1$–$C_6$-haloalkyl, $C_3$–$C_8$-cycloalkyl, phenyl-$C_1$–$C_3$-alkyl or phenyl where the phenyl rings may, if desired, furthermore carry from one to three of the radicals stated for $R^1$, or, if $R^6$ and $R^7$ are each alkyl or $R^6$ is alkyl and $R^7$ is a group —CO—H, —CO—($C_1$–$C_4$-alkyl), —CH=N—$R^{10}$ or —C($C_1$–$C_4$-alkyl)=N—$R^{10}$, $R^6$ and $R^7$ together form a 5-membered to 7-membered ring which is substituted by from one to four $C_1$–$C_4$-alkyl groups or is fused with a phenyl ring which may carry from one to three of the groups stated for $R^1$, and the agriculturally useful salts of the compounds I, where these compounds contain a basic nitrogen substituent or an acidic hydroxyl substituent, with the provisos that $R^6$ and $R^7$ are not simultaneously phenyl when m is zero, $R^6$ is not amino when $R^7$ is cyano or ethoxycarbonyl, $R^6$ is not hydroxyl when $R^7$ is ethoxycarbonyl and $R^6$ is not methyl when $R^7$ is methylcarbonyl.

The present invention furthermore relates to processes for the preparation of the compounds I and to herbicides which contain 2-(4-hetaryloxy)- or 2-(4-aryloxy)-phenoxyacetic or -propionic acid derivatives and/or cyclohexenone derivatives as herbicidal active ingredients and pyrido-fused 4-oxo-4H-benzopyrans I' (where I' has the meanings of I without the provisos) as antidotes, and to methods for selectively controlling undesirable plant growth with these herbicides.

The compounds I according to the invention are obtainable by various methods. 2-Amino-4-oxo-4H-benzopyran-3-carbaldehydes are obtained, for example, by formylating unsubstituted or substituted o-hydroxyacetophenones with phosphoryl chloride and dimethylformamide (H. Harnisch, Liebigs Ann. Chem. 765 (1972) 8; A. Nohara et al., Tetrahedron Lett. 1973, 1995), converting the aldehyde to the oxime, subjecting the latter to an alkali-catalyzed rearrangement reaction and then condensing the product with malonic acid derivatives (U. Petersen et al., Liebigs Ann. Chem. 1976, 1659). A crop-projecting effect of pyrido-fused 4-oxo-4H-benzopyrans is not mentioned in the prior art.

It was an object of the present invention to provide compounds which reduce the disadvantages encountered when using the abovementioned herbicides of the formulae V and VI at least to such an extent that the herbicides are tolerated by the crops from the grass family.

We have found that this object is achieved by the pyrido-fused 4-oxo-4H-benzopyrans I defined at the outset. We have also found processes for the preparation of these compounds and for the joint application of these compounds and compounds I' with the herbicides V and VI for influencing undesirable plant growth. The present invention furthermore relates to agents which contain the compounds I', whether the herbicidal active ingredient and the antidote compound are formulated and applied together or separately being unimportant and, in the case of separate application, the order in which the herbicidal active ingredient and the antidote are applied being irrelevant.

The novel compounds I are obtainable by a plurality of methods. Thus, pyrido-fused 4-oxo-4H-benzopyrans are obtained, for example according to the literature cited at the outset, by formylating 2-hydroxyacetophenone VII in an inert, aprotic, polar solvent with dimethylformamide/phosphoryl chloride, converting the aldehyde into the oxime and subjecting the latter to a rearrangement reaction under alkaline catalysis to give the o-aminoaldehyde II and fusing the latter with the ketone III in the presence of a base in an inert organic solvent.

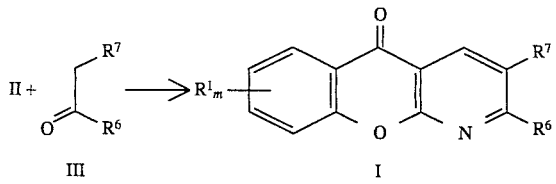

-continued

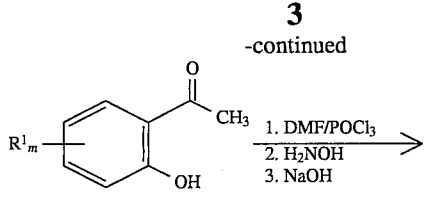

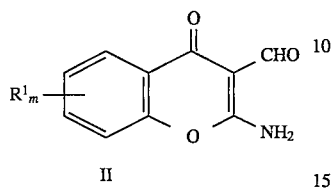

Usually, the starting materials VII and POCl₃ are used in a stoichiometric ratio. However, an excess of one or other may be entirely advantageous in specific cases.

The reaction can be carried out continuously or batchwise at atmospheric, superatmospheric or reduced pressure, by the conventional methods. The reaction temperature is in general from −10° to 100° C., in particular from 0° to 40° C.

The solvents used are, for example, aliphatic and aromatic chlorohydrocarbons, such as dichloromethane, chloroform or chlorobenzene, or dimethylformamide present in excess.

Examples of suitable solvents for the fusion with III are aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, relatively high-boiling ethers, such as tetrahydrofuran or dioxane, aliphatic alcohols, such as methanol, ethanol, propanol or isopropanol, and nitriles, such as acetonitrile and propionitrile.

The bases used are in particular aliphatic, aromatic or heterocyclic amines, for example triethylamine, dimethylamine, diisopropylamine, piperidine, dimethylaniline, dimethylbenzylamine, pyridine and 4-dimethylaminopyridine, hydroxides of alkali and alkaline earth metals, for example sodium hydroxide, potassium hydroxide or calcium hydroxide, alcoholates of alkali and alkaline earth metals, for example sodium methylate, sodium ethylate, calcium methylate or potassium tert-butylate, and alkali or alkaline earth metal hydrides, for example sodium hydride, potassium hydride or calcium hydride.

In certain circumstances, it may be advantageous to carry out the condensation in the presence of a conventional phase transfer catalyst.

In view of the intended use of the compounds I and I' as crop protection agents, suitable substituents are the following radicals:

m is 0, 1 or 2 and the radicals $R^1$ may be different when m is 2, $R^1$ is hydrogen, hydroxyl, nitro, halogen, such as fluorine, chlorine, bromine and iodine, in particular chlorine or bromine, $C_1$–$C_6$-alkyl, such as methyl, ethyl, propyl, 1-methylethyl, butyl, 1-methylpropyl and 1,1-dimethylethyl, particularly preferably methyl or ethyl, $C_1$–$C_6$-alkoxy, such as methoxy, ethoxy, propoxy, 1-methylethoxy, butoxy, 1-methylpropoxy, 2-methylpropoxy or hexyloxy, in particular methoxy or ethoxy, $C_1$–$C_6$-haloalkyl, in particular $C_1$- or $C_2$-haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoromethyl, 2-chloro-2,2-difluoroethyl, 2,2-dichloro- 2-fluoroethyl, 2,2,2-trichloroethyl and pentafluoroethyl, particularly preferably trichloromethyl or trifluoromethyl, $C_1$–$C_4$-haloalkoxy, in particular $C_1$- or $C_2$-haloalkoxy, such as difluoromethoxy, trifluoromethoxy, chlorodifluoromethoxy, dichlorofluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, particularly preferably 2,2,2-trifluoroethoxy, $C_1$–$C_4$-alkylthio, such as methylthio, ethylthio, propylthio, 1-methylethylthio, butylthio, 1-methylpropylthio, 2-methylpropylthio and 1,1-dimethylethylthio, in particular methylthio, or a group $NR^2R^3$, $R^2$ is hydrogen or $C_1$–$C_4$-alkyl, such as methyl, ethyl, n-propyl, isopropyl, n-butyl and tert-butyl, in particular methyl or ethyl, $R^3$ is hydrogen or $C_1$–$C_4$-alkyl, such as methyl, ethyl, n-propyl, isopropyl, butyl and tert-butyl, in particular methyl or ethyl, a group —CO—$R^4$, —CS—$R^4$, in particular acetyl- or propionyl, or a group —SO₂—$R^5$, in particular 4-methylsulfonyl, $R^4$ is $C_1$–$C_{20}$-alkyl, such as methyl, ethyl, n-propyl, isopropyl, n-butyl, tert-butyl, n-pentyl, n-hexyl, octyl, dodecyl, hexadecyl or octadecyl, preferably $C_1$–$C_6$-alkyl as stated for $R^1$, in particular methyl or ethyl, $C_1$–$C_6$-haloalkyl as stated for $R^1$, $C_3$–$C_8$-cycloalkyl, such as cyclopropyl, cyclobutyl, cyclopentyl, cyclohexyl, cycloheptyl and cyclooctyl, in particular cyclohexyl, phenyl-$C_1$–$C_3$-alkyl, such as benzyl, 2-phenylethyl or 3-phenylpropyl, in particular benzyl, amino which may carry one or two of the alkyl radicals stated for $R^1$, in particular methyl, where these radicals may be different in the case of disubstituted amino, in particular methylbenzylamino, aminophenyl where the phenyl ring may carry from one to three of the groups stated for $R^1$, and phenyl which may carry from one to three of the groups stated for $R^1$, $R^5$ is $C_1$–$C_4$-alkyl, such as methyl, ethyl, n-propyl, isopropyl, n-butyl and tert-butyl, in particular methyl or ethyl, or phenyl which may carry from one to three of the groups stated for $R^1$, $R^6$ is hydroxyl, $C_1$–$C_6$-alkoxy as stated for $R^1$, in particular methoxy or ethoxy, $C_1$–$C_6$-alkyl as stated for $R^1$, in particular methyl or ethyl, phenyl which may carry from one to three of the groups stated for $R^1$, a group —CO—$R^9$ or —CS—$R^9$, in particular CO—$R^9$, eg. 13 COOH, —CO—O($C_1$14 $C_4$-alkyl),

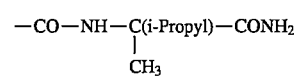

or $C_1$–$C_4$-alkyl-substituted 4-methyl-5-oxoimidazolin-2-yl, for example the group

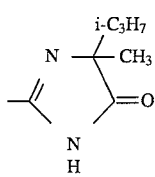

$R^7$ is cyano or $C_1$–$C_6$-alkyl as stated for $R^1$, in particular methyl, phenyl which may carry from one to three of the groups stated for $R^1$ or a group —CH=N—$R^{10}$, —C($C_1$–$C_4$-alkyl)=N—$R^{10}$, —CO—$R^{11}$ or —CS—$R^{11}$, $R^{10}$ is $C_1$–$C_4$-alkyl, such as methyl, ethyl, n-propyl, isopropyl, n-butyl and tert-butyl, $C_3$–$C_8$-cycloalkyl, such as cyclopropyl, cyclopentyl, cyclohexyl, cycloheptyl and cyclooctyl, in particular cyclohexyl, phenyl which may carry from one to three of the groups stated for $R^1$, hydroxyl, $C_1$–$C_8$-alkoxy as stated for $R^1$, or a group —O—CO-$R^{12}$ or —O—CS—$R^{12}$, $R^{12}$ is $C_1$–$C_{20}$-alkyl as stated for $R^4$, $C_1$4 $C_6$-haloalkyl as stated for $R^1$, in particular chloroethyl, $C_3$–$C_8$-cycloalkyl, such as cyclopropyl, cyclopentyl, cyclohexyl, cycloheptyl and cyclooctyl, in particular cyclohexyl, phenyl-$C_1$–$C_3$-alkyl, such as benzyl, 2-phenylethyl, 3-phenylpropyl and 2-phenylpropyl, in particular benzyl, or phenyl which may carry from one to three of the radicals stated for $R^1$, $R^9$ and $R^{11}$ are each $C_1$–$C_6$-alkyl as stated for $R^1$, in particular methyl, $C_1$–$C_6$-alkoxy as stated for $R^1$, in particular methoxy or ethoxy, hydroxyl, unsubstituted or alkyl-substituted amino as stated for $R^4$, branched $C_2$–$C_6$-alkyl which is substituted by an amido group $CONH_2$, for example

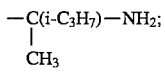

or aminophenyl where the phenyl ring may furthermore carry from one to three of the groups stated for $R^1$, or, if $R^6$ and $R^7$ are each alkyl or $R^6$ is alkyl and $R^7$ is a group —CO—H, —CO—($C_1$–$C_4$-alkyl), —CH=N—$R^{10}$ or —C($C_1$–$C_4$-alkyl)=N—$R^{10}$, $R^6$ and $R^7$ together form a 5-membered to 7-membered ring which is substituted by one to four $C_1$–$C_4$-alkyl groups or is fused with a phenyl ring which may carry from one to three of the groups stated for $R^1$.

Derivatives I and I' having acidic terminal groups or having basic nitrogen atoms may be present in the form of their agriculturally useful salts.

Suitable acid addition salts are the salts of acids which do not adversely affect the antidote activity of I, for example the hydrochlorides and hydrobromides, sulfates, nitrates, phosphates, oxalates or the dodecylbenzenesulfonates.

Suitable basic salts are salts of bases which do not adversely affect the antidote activity of I, for example the alkali metal salts, in particular sodium and potassium salts, the alkaline earth metal salts, in particular calcium, magnesium and barium salts, transition metal salts, in particular manganese, copper, zinc and iron salts, ammonium salts which may carry from one to three $C_1$–$C_4$-alkyl or hydroxy-$C_1$–$C_4$-alkyl substituents and/or a phenyl or benzyl substituent, in particular diisopropylammonium, tetramethylammonium, tetrabutylammonium, trimethylbenzylammonium and trimethyl-(2-hydroxyethyl-)ammonium salts, the phosphonium salts, the sulfonium salts, in particular tri-$C_1$–$C_4$-alkylsulfonium salts, and the sulfoxonium salts, in particular tri-$C_1$–$C_4$-alkylsulfoxonium salts.

The pyrido-fused 4-oxo-4H-benzopyrans I and I' are suitable as antidotes for ensuring that herbicidal active ingredients are better tolerated by crops such as millet, rice, corn, cereal species (wheat, rye, barley and oats), cotton, sugar beet, sugar cane and soybean. They have an antagonistic effect on herbicides of a very wide range of classes, such as triazines, phenylurea derivatives, carbamates, thiocarbamates, haloacetanilides, benzoic acid derivatives and in particular halophenoxyacetates, substituted phenoxyphenoxy acetates, phenoxyphenoxypropionates and cyclohexenone derivatives.

Herbicidal active ingredients from the group consisting of the 2-(4-hetaryloxy)- or 2-(4-aryloxy)phenoxyacetic acid derivatives of the formula V

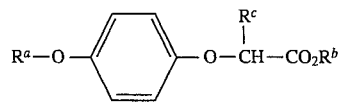

where $R^a$ is phenyl, pyridyl or benzoxazyl, $R^b$ is hydrogen, $C_1$–$C_4$-alkyl or the equivalent [sic], $R^c$ is hydrogen or methyl, are known from the literature, for example from DE-A-22 23 894, DE-A-24 33 067, DE-A-25 76 251, DE-A-30 04 770, BE-A-868 875 and BE-A-858 618.

They are used for controlling undesirable plants from the Gramineae family. However, the toleration of these substances by crops varies from commercially acceptable to non-tolerated, depending on the substituents and application rates.

The same situation is encountered with cyclohexenone derivatives of the formula VI

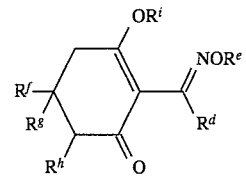

where $R^d$ is $C_1$–$C_4$-alkyl, such as methyl, ethyl, n-propyl, isopropyl, n-butyl and tert-butyl, preferably ethyl or n-propyl, $R^e$ is $C_1$–$C_4$-alkyl, such as methyl, ethyl, n-propyl, isopropyl, n-butyl and tert-butyl, preferably ethyl or n-propyl, $C_3$- or $C_4$-alkenyl, preferably prop-2-enyl, $C_3$- or $C_4$-alkynyl or $C_3$- or $C_4$-haloalkenyl, preferably 3-chloroprop-2-en-1-yl, a $C_2$–$C_4$-alkylene or $C_3$- or $C_4$-alkenylene chain, both of which may furthermore carry from one to three $C_1$–$C_3$-alkyl radicals and/or halogen atoms, or a 3-membered to 6-membered alkylene chain or a 4-membered to 6-membered alkenylene chain which, if desired, is substituted by $C_1$–$C_3$-alkyl and each of which contains, as a chain member, an oxygen or sulfur atom which is not directly adjacent to the oxime ether moiety, all abovementioned chains carrying a terminal phenyl ring which in turn may be substituted by from one to three radicals selected from the group consisting of one benzyloxycarbonyl or phenyl radical and from one to three of each of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring additionally to carry a number of halogen atoms such that the total number of the radicals is 4 or 5; 4-(p-fluorophenyl)-but-3-enyl, 4-(p-chlorophenyl)-but- 3-enyl and 2-(p-chlorophenoxy)-propyl are particularly preferred;

thienyl which may furthermore carry a halogen atom;

$R^f$ is $C_1$–$C_4$-alkyl as stated for $R^d$, which may be monosubstituted or disubstituted by $C_1$–$C_4$-alkylthio or $C_1$–$C_4$-alkoxy, a 5-membered or 6-membered saturated or monounsaturated ring system which, in addition to carbon members, may contain one oxygen or one sulfur atom or a sulfoxyl or sulfonyl group, preferably tetrahydropyranyl, dihydropyranyl or tetrahydrothiopyranyl, where the ring system may furthermore carry from one to three radicals selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio, a 10-membered saturated or monounsaturated heterocyclic structure which contains two nonadjacent oxygen atoms or sulfur atoms and which may be substituted by up to three $C_1$–$C_4$-alkyl groups and/or methoxy groups, phenyl, pyridyl, thiazolyl or pyrazolyl, pyrrolyl or isoxazolyl, where these groups may each carry from one to three radicals selected from the group consisting of $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$$C_3$-alkyl, $C_1$–$C_4$-dialkoxy-$C_1$–$C_3$-alkyl, formyl, halogen and benzoylamino, $R^g$ is hydrogen or hydroxyl or, if $R^f$ is $C_1$–$C_6$-alkyl, $R^g$ is $C_1$–$C_6$-alkyl, preferably hydrogen, $R^h$ is hydrogen, cyano, halogen, $C_1$–$C_4$-alkoxycarbonyl or $C_1$–$C_4$-alkylketoxime, preferably hydrogen, and $R^i$ is hydrogen or one equivalent of an agriculturally useful cation.

They are likewise described in the literature (for example EP-A 228 598, EP-A 230 235, EP-A 238 021, EP-A 368 227, U.S. Pat. No. 4,432,786, DE-A 24 39 104, DE-A 40 14 986 and DE-A 40 33 423) as herbicides and are used predominantly for controling undesirable grasses in dicotyledon crops and in grasses which do not belong to the Gramineae family. Depending on the structure of the substituents and the dose used, compounds of this group can also be employed for selectively controlling undesirable grasses in gramineous crops, such as wheat and rice.

Cyclohexenone derivatives of the formula VI in which $R^e$ is unsubstituted or substituted alkyl- or alkenylphenyl, eg. butyl- or butenylphenyl, can be prepared in a conventional manner from already known derivatives of the formula VII (EP-A-80 301, EP-A-125 094, EP-A 142 741, U.S. Pat. No. 4,249,937, EP-A 137 174 and EP-A 177 913) and the corresponding hydroxylamines of the formula VIII (Houben-Weyl, 10/1, page 1181 et seq.) (EP-A 169 521).

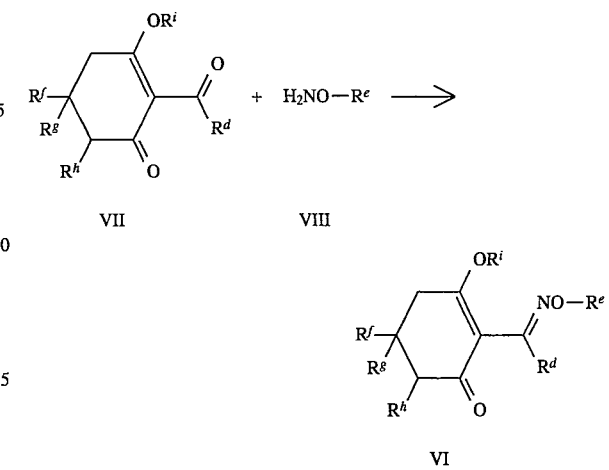

The reaction is expediently carried out in the heterogeneous phase in a solvent at an adequate temperature below about 80° C., in the presence of a base, and the hydroxylamine VIII is used in the form of its ammonium salt.

Examples of suitable bases are carbonates, bicarbonates, acetates, alcoholates or oxides of alkali or alkaline earth metals, in particular sodium hydroxide, potassium hydroxide, magnesium oxide and calcium oxide. Organic bases, such as pyridine or tertiary amines, may also be used. The base is added, for example, in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The product can be isolated, for example, by evaporating down the mixture, partitioning the residue between methylene chloride and water and distilling off the solvent under reduced pressure.

However, the free hydroxylamine base, for example in the form of an aqueous solution, can also be used directly for this reaction; a one-phase or two-phase reaction mixture is obtained, depending on the solvent used for the compound VII.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds VI can be obtained by treating the 3-hydroxy compounds with sodium hydroxide, potassium hydroxide, a sodium alcoholate or a potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts by means of ammonia or ammonium, phosphonium, sulfonium or sulfoxonium hydroxides.

The compounds of type VII can be prepared, for example from the corresponding cyclohexane-1,3-diones of the formula IX

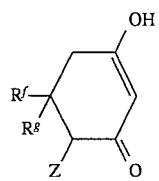

where Z is hydrogen or methoxycarbonyl and
R$^g$ is hydrogen,
by known methods (Tetrahedron Lett. (1975), 2491).

It is also possible to prepare the compounds of the formula VII via the enol ester intermediates which are obtained in the reaction of compounds of the formula IX with acyl chlorides in the presence of bases and are then subjected to a rearrangement reaction with certain imidazole or pyridine derivatives (Japanese Preliminary Published Application 79/063 052).

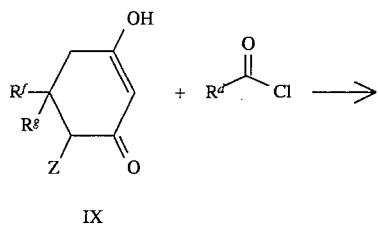

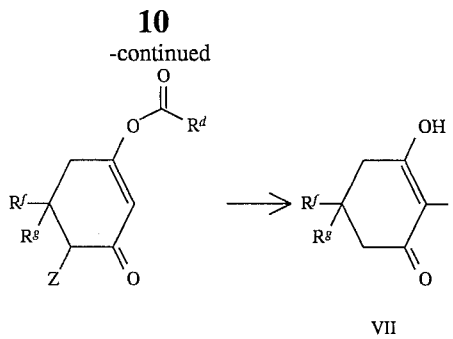

The compounds of the formula IX are obtained via a number of known process steps starting from known intermediates.

The synthesis of the hydroxylamines VIII in which R$^e$ is unsubstituted or substituted phenylbutyl is carried out according to the following reaction scheme, for example by α) alkylating cyclic hydroximides X with suitable phenylbutyl halides and then eliminating the protective group, for example with hydrazine or ethanolamine, similarly to Examples from EP-A-244 786 or Houben-Weyl, Methoden der organischen Chemie, Volume X/1, page 1152 et seq.

β) hydrogenating N-4-phenylbutenyloxyphthalimides, the preparation of which is described in DE-A 38 38 310, by means of suitable catalysts, for example palladium on active carbon, in suitable inert solvents, for example methanol, tetrahydrofuran or dioxane, and subsequently eliminating the protective group as described above.

The hydrogenation is advantageously carried out at from 20° C. to the boiling point of the solvent, in particular at room temperature, by the conventional methods, at atmospheric, superatmospheric or reduced pressure. A pressure of from 1 to 10, in particular from 1 to 2, bar is preferred.

Reaction scheme:

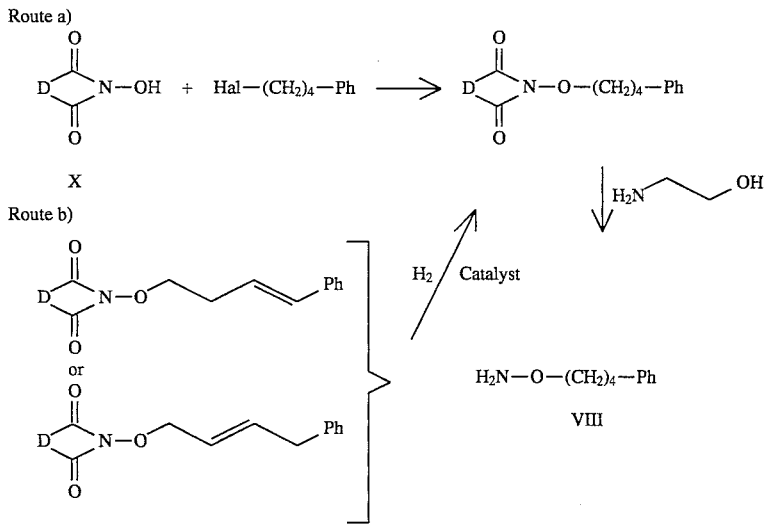

Ph=unsubstituted or substituted phenyl

Examples of suitable cyclic hydroximides X are the following substances:

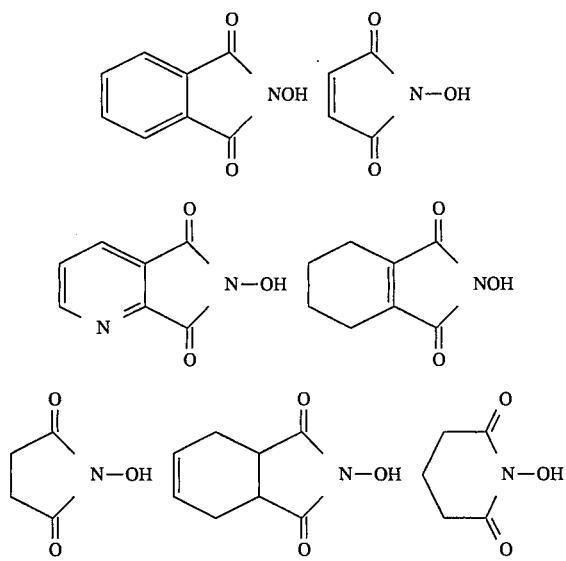

The synthesis of the hydroxylamines VIII in which $R^e$ is unsubstituted or substituted butenylphenyl, where the phenyl radical abbreviated to Ph below may in turn be substituted or unsubstituted, is carried out by the following reaction scheme, starting from aniline derivatives, by diazotization and subsequent coupling of the diazonium salt with an appropriately substituted butadiene XI. The resulting mixture of XIIa and XIIb is coupled to a cyclic hydroximide XIV and the protected hydroxylamine derivative XIII obtained is cleaved with 2-aminoethanol to give the free hydroxylamine VIII:

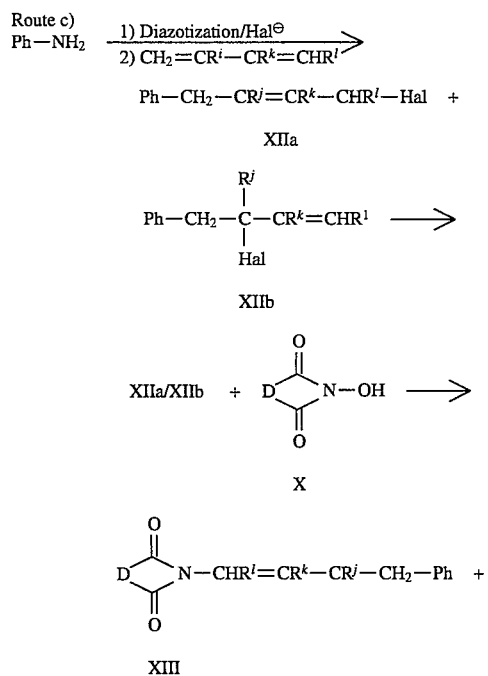

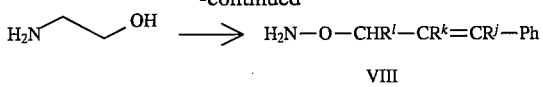

$R^j$, $R^k$ and $R^l$ independently of one another are each hydrogen, $C_1$–$C_3$-alkyl and/or halogen. Hal is halogen, preferably chlorine.

The halides XIIa required for the above synthesis of the hydroxylamines of the formula VIII can be prepared, as a mixture with XIIb, by processes known from the literature, for example by reacting diazonium salts of aromatic and heteroaromatic anilines with dienes. The range of applications of the reaction is discussed in Organic Reactions 11 (1960), 189 and 24 (1976), 225.

Coupling of the isomeric halides XIIa and XIIb with a cyclic hydroximide of the formula X gives exclusively the cyclic imidoethers of the formula XIII which, after elimination of the protective group on the nitrogen, give the hydroxylamines VIII.

The reaction with a hydroximide X (routes a and c) is carried out in the presence of an acid acceptor and of a solvent. For cost reasons, hydroxyphthalimide is preferably used as the hydroximide X.

Suitable acid acceptors are alkali metal carbonates, such as potassium carbonate or sodium carbonate, alkali metal bicarbonates, such as potassium bicarbonate and sodium bicarbonate, tertiary amines, such as trimethylamine and triethylamine, and basic heterocycles, such as pyridine. For cost reasons, potassium carbonate and sodium carbonate are preferred.

Suitable solvents are aprotic dipolar organic solvents, for example dimethylformamide, dimethyl sulfoxide and/or sulfolane.

Alkylation under phase transfer conditions is also possible. The organic solvents used here are water-immiscible compounds, such as hydrocarbons or chlorohydrocarbons. Suitable phase transfer catalysts are quaternary ammonium and phosphonium salts.

The cleavage of the cyclic imidoethers XIII is carried out by a process similar to that described in EP-A 244 786, using alkanolamines. In this process, the hydroxylamines VIII can be isolated as free bases or, after precipitation with acids, in the form of salts. Readily crystallizing salts are obtained by reacting the bases with oxalic acid.

Specific examples of herbicidal hetaryloxy- or aryloxyphenoxyacetic acid derivatives of the formula V whose toleration by crops can be improved by means of pyrido-fused 4-oxo-4H-benzopyrans of the formula I or I' are shown in Table 1 below.

TABLE 1

$$R^a\text{—}O\text{—}\underset{}{\phantom{X}}\text{—}O\text{—}\underset{R^c}{\underset{|}{CH}}\text{—}CO_2R^b \quad V$$

| No. | $R^a$ | $R^b$ | $R^c$ | Reference |
|---|---|---|---|---|
| 1.01 | (dichlorophenyl) | $CH_3$ | $CH_3$ | DE-A 22 23 894 |

TABLE 1-continued $$R^a-O-\underset{}{\bigodot}-O-\underset{R^c}{\overset{}{\underset{|}{CH}}}-CO_2R^b \quad V$$

| No. | R$^a$ | R$^b$ | R$^c$ | Reference |
|---|---|---|---|---|
| 1.02 | 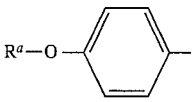 | n-C$_4$H$_9$ | CH$_3$ | BE-A 868 875 |
| 1.03 | 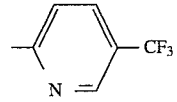 | C$_2$H$_5$ | CH$_3$ | BE-A 858 618 |
| 1.04 | 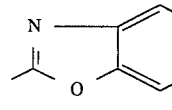 | CH$_3$ | CH$_3$ | BE-A 868 875 |
| 1.05 | 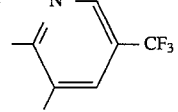 | C$_2$H$_5$ | CH$_3$ | DE-A 30 04 770 |

Specific examples of cyclohexenones of the formula VI whose toleration by plants can be improved by pyrido-fused 4-oxo-4H-benzopyrans I and I' are shown in Tables 2 to 13 below.

TABLE 2

$$VI \quad (R^3 = -CH_2CH_2-O-\underset{}{\bigodot}-\text{Radicals}) \quad ; R^g, R^h, R^i = H$$

| No. | R$^d$ | R$^f$ | Radicals on phenyl ring | Physical data/$^1$H-NMR [δ in ppm], mp. [°C.] |
|---|---|---|---|---|
| 2.01 | Ethyl | Tetrahydropyran-3-yl | — | 42–45 |
| 2.02 | Propyl | Tetrahydropyran-3-yl | — | 3,90 (m, 2H), 4,20 (t, 2H), 4,40 (m, 2H), 6,80–7,00 (m, 3H), 7,13–7,37 (m, 2H) |
| 2.03 | Ethyl | Tetrahydropyran-4-yl | — | 106–107 |
| 2.04 | Propyl | Tetrahydropyran-4-yl | — | 72–73 |
| 2.05 | Ethyl | Tetrahydrothiopyran-3-yl | — | 52–55 |
| 2.06 | Propyl | Tetrahydrothiopyran-3-yl | — | 92 |
| 2.07 | Ethyl | Tetrahydropyran-3-yl | 2-F | 76–78 |
| 2.08 | Propyl | Tetrahydropyran-3-yl | 2-F | 72–77 |
| 2.09 | Ethyl | Tetrahydropyran-4-yl | 2-F | 121–125 |
| 2.10 | Propyl | Tetrahydropyran-4-yl | 2-F | 103–107 |
| 2.11 | Ethyl | Tetrahydrothiopyran-3-yl | 2-F | 82–86 |
| 2.12 | Propyl | Tetrahydrothiopyran-3-yl | 2-F | 81–85 |
| 2.13 | Ethyl | Tetrahydropyran-3-yl | 3-F | 62–68 |
| 2.14 | Propyl | Tetrahydropyran-3-yl | 3-F | 3,90 (m, 2H), 4,20 (t, 2H), 4,40 (m, 2H) 6,70 (m, 3H), 7,25 (m, 1H), |
| 2.15 | Ethyl | Tetrahydropyran-4-yl | 3-F | 103–109 |
| 2.16 | Propyl | Tetrahydropyran-4-yl | 3-F | 73–79 |
| 2.17 | Ethyl | Tetrahydrothiopyran-3-yl | 3-F | 4,20 (t, 2H), 4,40 (m, 2H) 6,70 (m, 3H), 7,25 (m, 1H) |
| 2.18 | Propyl | Tetrahydrothiopyran-3-yl | 3-F | |
| 2.19 | Ethyl | Tetrahydropyran-3-yl | 4-F | 64–67 |
| 2.20 | Propyl | Tetrahydropyran-3-yl | 4-F | 70–72 |
| 2.21 | Ethyl | Tetrahydropyran-4-yl | 4-F | 101–103 |
| 2.22 | Propyl | Tetrahydropyran-4-yl | 4-F | 107–109 |
| 2.23 | Ethyl | Tetrahydrothiopyran-3-yl | 4-F | 105–108 |
| 2.24 | Propyl | Tetrahydrothiopyran-3-yl | 4-F | 82–84 |
| 2.25 | Ethyl | Tetrahydropyran-3-yl | 2-Cl | 74–80 |
| 2.26 | Propyl | Tetrahydropyran-3-yl | 2-Cl | 67–71 |
| 2.27 | Ethyl | Tetrahydropyran-4-yl | 2-Cl | 4,00 (m, 2H), 4,27 (t, 2H), 4,47 (m, 2H), 7,20 (t, 1H), 7,37 (d, 1H) |
| 2.28 | Propyl | Tetrahydropyran-4-yl | 2-Cl | 68–72 |
| 2.29 | Ethyl | Tetrahydrothiopyran-3-yl | 2-Cl | 74–78 |
| 2.30 | Propyl | Tetrahydrothiopyran-3-yl | 2-Cl | 72–78 |
| 2.31 | Ethyl | Tetrahydropyran-3-yl | 3-Cl | |
| 2.32 | Propyl | Tetrahydropyran-3-yl | 3-Cl | |
| 2.33 | Ethyl | Tetrahydropyran-4-yl | 3-Cl | |
| 2.34 | Propyl | Tetrahydropyran-4-yl | 3-Cl | |

TABLE 2-continued

VI ($R^3 = -CH_2CH_2-O-$⟨phenyl⟩—Radicals ; $R^g, R^h, R^i = H$)

Structure: $R^f$—(cyclohexenone with OH, $R^d$, =NO—$CH_2CH_2O$—phenyl—Radicals)

| No. | $R^d$ | $R^f$ | Radicals on phenyl ring | Physical data/$^1$H-NMR [δ in ppm], mp. [°C.] |
|---|---|---|---|---|
| 2.35 | Ethyl | Tetrahydrothiopyran-3-yl | 3-Cl | |
| 2.36 | Propyl | Tetrahydrothiopyran-3-yl | 3-Cl | |
| 2.37 | Ethyl | Tetrahydropyran-3-yl | 4-Cl | 3,93 (m, 2H), 4,20 (t, 2H), 4,43 (m, 2H), 6,90 (m, 2H), 7,25 (m, 2H) |
| 2.38 | Propyl | Tetrahydropyran-3-yl | 4-Cl | 3,93 (m, 2H), 4,20 (t, 2H), 4,43 (m, 2H), 6,90 (m, 2H), 7,25 (m, 2H) |
| 2.39 | Ethyl | Tetrahydropyran-4-yl | 4-Cl | 116–118 |
| 2.40 | Propyl | Tetrahydropyran-4-yl | 4-Cl | 104–106 |
| 2.41 | Ethyl | Tetrahydrothiopyran-3-yl | 4-Cl | 74–77 |
| 2.42 | Propyl | Tetrahydrothiopyran-3-yl | 4-Cl | 86–88 |
| 2.43 | Ethyl | Tetrahydropyran-3-yl | 2-CF$_3$ | |
| 2.44 | Propyl | Tetrahydropyran-3-yl | 2-CF$_3$ | |
| 2.45 | Ethyl | Tetrahydropyran-4-yl | 2-CF$_3$ | |
| 2.46 | Propyl | Tetrahydropyran-4-yl | 2-CF$_3$ | |
| 2.47 | Ethyl | Tetrahydrothiopyran-3-yl | 2-CF$_3$ | |
| 2.48 | Propyl | Tetrahydrothiopyran-3-yl | 2-CF$_3$ | |
| 2.49 | Ethyl | Tetrahydropyran-3-yl | 3-CF$_3$ | |
| 2.50 | Propyl | Tetrahydropyran-3-yl | 3-CF$_3$ | |
| 2.51 | Ethyl | Tetrahydropyran-4-yl | 3-CF$_3$ | |
| 2.52 | Propyl | Tetrahydropyran-4-yl | 3-CF$_3$ | |
| 2.53 | Ethyl | Tetrahydrothiopyran-3-yl | 3-CF$_3$ | |
| 2.54 | Propyl | Tetrahydrothiopyran-3-yl | 3-CF$_3$ | |
| 2.55 | Ethyl | Tetrahydropyran-3-yl | 4-CF$_3$ | 72–77 |
| 2.56 | Propyl | Tetrahydropyran-3-yl | 4-CF$_3$ | 3,90 (m, 2H), 4,27 (t, 2H), 4,47 (m, 2H) 7,00 (d, 2H), 7,55 (d, 2H) |
| 2.57 | Ethyl | Tetrahydropyran-4-yl | 4-CF$_3$ | |
| 2.58 | Propyl | Tetrahydropyran-4-yl | 4-CF$_3$ | 90–94 |
| 2.59 | Ethyl | Tetrahydrothiopyran-3-yl | 4-CF$_3$ | 73–79 |
| 2.60 | Propyl | Tetrahydrothiopyran-3-yl | 4-CF$_3$ | 4,27 (t, 2H), 4,47 (m, 2H), 7,00 (d, 2H) 7,55 (d, 2H) |
| 2.61 | Ethyl | Tetrahydropyran-3-yl | 2,4-Cl$_2$ | 73–75 |
| 2.62 | Propyl | Tetrahydropyran-3-yl | 2,4-Cl$_2$ | 69–73 |
| 2.63 | Ethyl | Tetrahydropyran-4-yl | 2,4-Cl$_2$ | 4,00 (m, 2H), 4,25 (t, 2H), 4,45 (t, 2H) 6,87 (d, 1H), 7.17 (d, 1H), 7,37 (d, 1H) |
| 2.64 | Propyl | Tetrahydropyran-4-yl | 2,4-Cl$_2$ | 4,00 (m, 2H), 4,25 (t, 2H), 4,45 (t, 2H) 6,87 (d, 1H), 7,17 (d, 1H), 7,37 (d, 1H) |
| 2.65 | Ethyl | Tetrahydrothiopyran-3-yl | 2,4-Cl$_2$ | 4,25 (t, 2H), 4,45 (t, 2H), 6,87 (d, 1H) 7,17 (d, 1H), 7,37 (d, 1H) |
| 2.66 | Propyl | Tetrahydrothiopyran-3-yl | 2,4-Cl$_2$ | 4,25 (t, 2H), 4,45 (t, 2H), 6,87 (d, 1H) 7,17 (d, 1H), 7,37 (d, 1H) |
| 2.67 | Ethyl | Tetrahydropyran-3-yl | 2,4,6-Cl$_3$ | 90–93 |
| 2.68 | Propyl | Tetrahydropyran-3-yl | 2,4,6-Cl$_3$ | 83–87 |
| 2.69 | Ethyl | Tetrahydropyran-4-yl | 2,4,6-Cl$_3$ | 79–82 |
| 2.70 | Propyl | Tetrahydropyran-4-yl | 2,4,6-Cl$_3$ | 4,00 (m, 2H), 4,27 (t, 2H), 4,45 (m, 2H), 7,32 (s, 2H) |
| 2.71 | Ethyl | Tetrahydrothiopyran-3-yl | 2,4,6-Cl$_3$ | 105–108 |
| 2.72 | Propyl | Tetrahydrothiopyran-3-yl | 2,4,6-Cl$_3$ | 4,27 (t, 2H), 4,45 (m, 2H), 7,82 (s, 2H) |
| 2.73 | Ethyl | Tetrahydropyran-3-yl | 4-NO$_2$ | 3,90 (m, 2H), 4,32 (m, 2H), 4,50 (m, 2H), 7,00 (d, 2H), 8,20 (d, 2H) |
| 2.74 | Propyl | Tetrahydropyran-3-yl | 4-NO$_2$ | 3,90 (m, 2H), 4,32 (m, 2H), 4,50 (m, 2H) 7,00 (d, 2H), 8,20 (d, 2H) |
| 2.75 | Ethyl | Tetrahydropyran-4-yl | 4-NO$_2$ | 126–129 |
| 2.76 | Propyl | Tetrahydropyran-4-yl | 4-NO$_2$ | 138–141 |
| 2.77 | Ethyl | Tetrahydrothiopyran-3-yl | 4-NO$_2$ | 4,32 (m, 2H), 4,50 (m, 2H), 7,00 (d, 2H), 8,20 (d, 2H) |
| 2.78 | Propyl | Tetrahydrothiopyran-3-yl | 4-NO$_2$ | 4,32 (m, 2H), 4,50 (m, 2H), 7,00 (d, 2H) 8,20 (d, 2H) |

TABLE 3

$R^f$ — [structure: cyclohexenone with OH, NO—CH₂CH(CH₃)—O—phenyl with Radicals, R^d] VI ($R^e$ = —CH₂CH(CH₃)—O—phenyl with Radicals; $R^g, R^h, R^i$ = H)

| No. | $R^d$ | $R^f$ | Radicals on phenyl ring | Physical data/¹H-NMR [δ in ppm], mp. [°C.] |
|---|---|---|---|---|
| 3.01 | Ethyl | Tetrahydropyran-3-yl | — | |
| 3.02 | Propyl | Tetrahydropyran-3-yl | — | |
| 3.03 | Ethyl | Tetrahydropyran-4-yl | — | |
| 3.04 | Propyl | Tetrahydropyran-4-yl | — | |
| 3.05 | Ethyl | Tetrahydrothiopyran-3-yl | — | |
| 3.06 | Propyl | Tetrahydrothiopyran-3-yl | — | |
| 3.07 | Ethyl | Tetrahydropyran-3-yl | 4-F | |
| 3.08 | Propyl | Tetrahydropyran-3-yl | 4-F | |
| 3.09 | Ethyl | Tetrahydropyran-4-yl | 4-F | |
| 3.10 | Propyl | Tetrahydropyran-4-yl | 4-F | |
| 3.11 | Ethyl | Tetrahydrothiopyran-3-yl | 4-F | |
| 3.12 | Propyl | Tetrahydrothiopyran-3-yl | 4-F | |
| 3.13 | Ethyl | Tetrahydropyran-3-yl | 4-Cl | |
| 3.14 | Propyl | Tetrahydropyran-3-yl | 4-Cl | |
| 3.15 | Ethyl | Tetrahydropyran-4-yl | 4-Cl | 1,35 (m, 3H), 4,05–4,30 (m, 2H), 4,60 (m, 1H), 6,80–7,40 (m, 4H) |
| 3.16 | Propyl | Tetrahydropyran-4-yl | 4-Cl | 1,35 (m, 3H), 4,05–4,30 (m, 2H), 4,60 (m, 1H), 6,80–7,40 (m, 4H) |
| 3.17 | Ethyl | Tetrahydrothiopyran-3-yl | 4-Cl | 1,35 (m, 3H), 4,05–4,25 (m, 2H), 4,60 (m, 1H), 6,80–7,40 (m, 4H) |
| 3.18 | Propyl | Tetrahydrothiopyran-3-yl | 4-Cl | 1,35 (m, 3H), 4,05–4,30 (m, 2H), 4,60 (m, 1H), 6,80–7,40 (m, 4H) |

TABLE 4

$R^f$ — [structure: cyclohexenone with OH, NO—CH₂CH₂—S—phenyl with Radicals, R^d] VI ($R^e$ = —CH₂CH₂—S—phenyl with Radicals; $R^g, R^h, R^i$ = H)

| No. | $R^d$ | $R^f$ | Radicals on phenyl ring | Physical/data ¹H-NMR [δ in ppm], mp. [°C.] |
|---|---|---|---|---|
| 4.01 | Ethyl | Tetrahydropyran-3-yl | — | 3,90 (m, 2H), 4,23 (t, 2H), 7,17–7,43 (m, 5H) |
| 4.02 | Propyl | Tetrahydropyran-3-yl | — | 65 |
| 4.03 | Ethyl | Tetrahydropyran-4-yl | — | 3,97 (m, 2H), 4,23 (t, 2H), 7,17–47,43 (m, 5H) |
| 4.04 | Propyl | Tetrahydropyran-4-yl | — | 3,97 (m, 2H), 4,23 (t, 2H), 7,17–47,43 (m, 5H) |
| 4.05 | Ethyl | Tetrahydrothiopyran-3-yl | — | 4,23 (t, 2H), 7,17–7,43 (m, 5H) |
| 4.06 | Propyl | Tetrahydrothiopyran-3-yl | — | 4,23 (t, 2H), 7,17–7,43 (m, 5H) |
| 4.07 | Ethyl | Tetrahydropyran-3-yl | 4-F | 3,90 (m, 2H), 4,17 (t, 2H), 7,00 (m, 2H), 7,40 (m, 2H) |
| 4.08 | Propyl | Tetrahydropyran-3-yl | 4-F | 3,90 (m, 2H), 4,17 (t, 2H), 7,00 (m, 2H), 7,40 (m, 2H) |
| 4.09 | Ethyl | Tetrahydropyran-4-yl | 4-F | 4,00 (m, 2H), 4,17 (t, 2H), 7,00 (m, 2H), 7,40 (m, 2H) |
| 4.10 | Propyl | Tetrahydropyran-4-yl | 4-F | 4,00 (m, 2H), 4,17 (t, 2H), 7,00 (m, 2H), 7,40 (m, 2H) |
| 4.11 | Ethyl | Tetrahydrothiopyran-3-yl | 4-F | 4,17 (t, 2H), 7,00 (m, 2H), 7,40 (m, 2H), |
| 4.12 | Propyl | Tetrahydrothiopyran-3-yl | 4-F | 4,17 (t, 2H), 7,00 (m, 2H), 7,40 (m, 2H), |
| 4.13 | Ethyl | Tetrahydropyran-3-yl | 4-Cl | 71–75 |
| 4.14 | Propyl | Tetrahydropyran-3-yl | 4-Cl | 63–65 |
| 4.15 | Ethyl | Tetrahydropyran-4-yl | 4-Cl | 4,00 (m, 2H), 4,20 (t, 2H), 7,30 (m, 4H) |
| 4.16 | Propyl | Tetrahydropyran-4-yl | 4-Cl | 4,00 (m, 2H), 4,20 (t, 2H), 7,30 (m, 4H) |
| 4.17 | Ethyl | Tetrahydrothiopyran-3-yl | 4-Cl | 4,20 (t, 2H), 7,30 (m, 4H) |
| 4.18 | Propyl | Tetrahydrothiopyran-3-yl | 4-Cl | 4,20 (t, 2H), 7,30 (m, 4H) |
| 4.19 | Ethyl | Tetrahydropyran-3-yl | 2-Cl | 3,90 (m, 2H), 4,25 (t, 2H), 7,10–7,50 (m, 4H) |
| 4.20 | Propyl | Tetrahydropyran-3-yl | 2-Cl | 3,90 (m, 2H), 4,25 (t, 2H), 7,10–7,50 (m, 4H) |
| 4.21 | Ethyl | Tetrahydropyran-4-yl | 2-Cl | 4,00 (m, 2H), 4,25 (t, 2H), 7,10–7,50 (m, 4H) |
| 4.22 | Propyl | Tetrahydropyran-4-yl | 2-Cl | 4,00 (m, 2H), 4,25 (t, 2H), 7,10–7,50 (m, 4H) |
| 4.23 | Ethyl | Tetrahydrothiopyran-3-yl | 2-Cl | 4,25 (t, 2H) 7,10–7,50 (m, 4H) |

TABLE 4-continued

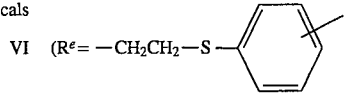

| No. | $R^d$ | $R^f$ | Radicals on phenyl ring | Physical/data $^1$H-NMR [δ in ppm], mp. [°C.] |
|---|---|---|---|---|
| 4.24 | Propyl | Tetrahydropyran-3-yl | 2-Cl | 4,25 (t, 2H) 7,10–7,50 (m, 4H) |
| 4.25 | Ethyl | Tetrahydropyran-3-yl | 2,6-Cl$_2$ | 3,90 (m, 2H) 4,20 (t, 2H), 7,20 (t, 1H) 7,40 (d, 2H) |
| 4.26 | Propyl | Tetrahydropyran-3-yl | 2,6-Cl$_2$ | 3,90 (m, 2H) 4,20 (t, 2H), 7,20 (t, 1H) 7,40 (d, 2H) |
| 4.27 | Ethyl | Tetrahydropyran-4-yl | 2,6-Cl$_2$ | 61–64 |
| 4.28 | Propyl | Tetrahydropyran-4-yl | 2,6-Cl$_2$ | 4,00 (m, 2H) 4,20 (t, 2H), 7,20 (t, 1H) 7,40 (d, 2H) |
| 4.29 | Ethyl | Tetrahydrothiopyran-3-yl | 2,6-Cl$_2$ | 4,20 (t, 2H) 7,20 (t, 2H), 7,40 (d, 2H) |
| 4.30 | Propyl | Tetrahydrothiopyran-3-yl | 2,6-Cl$_2$ | 4,20 (t, 2H) 7,20 (t, 2H), 7,40 (d, 2H) |

TABLE 5

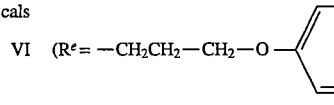

| No. | $R^d$ | $R^f$ | Radicals on phenyl ring | Physical data/$^1$H-NMR [δ in ppm], mp. [°C.] |
|---|---|---|---|---|
| 5.01 | Ethyl | Tetrahydropyran-3-yl | — | 3,90 (m, 2H), 4,03 (t, 2H), 4,23 (t, 2H), 6,90 (m, 3H), 7,27 (m, 2H) |
| 5.02 | Propyl | Tetrahydropyran-3-yl | — | 3,90 (m, 2H), 4,03 (t, 2H), 4,23 (t, 2H), 6,90 (m, 3H), 7,27 (m, 2H) |
| 5.03 | Ethyl | Tetrahydropyran-4-yl | — | 3,97 (m, 2H), 4,03 (t, 2H), 4,23 (t, 2H), 6,90 (m, 3H), 7,27 (m, 2H) |
| 5.04 | Propyl | Tetrahydropyran-4-yl | — | 3,97 (m, 2H), 4,03 (t, 2H), 4,23 (t, 2H), 6,90 (m, 3H), 7,27 (m, 2H) |
| 5.05 | Ethyl | Tetrahydrothiopyran-3-yl | — | 4,03 (t, 2H), 4,23 (t, 2H), 6,90 (m, 3H), 7,27 (m, 2H) |
| 5.06 | Propyl | Tetrahydrothiopyran-3-yl | — | 4,03 (t, 2H), 4,23 (t, 2H), 6,90 (m, 3H), 7,27 (m, 2H) |
| 5.07 | Ethyl | Tetrahydropyran-3-yl | 2-F | 3,90 (m, 2H), 4,10 (t, 2H), 4,27 (t, 2H), 6,80–7,15 (m, 4H) |
| 5.08 | Propyl | Tetrahydropyran-3-yl | 2-F | 3,90 (m, 2H), 4,10 (t, 2H), 4,27 (t, 2H), 6,80–7,15 (m, 4H) |
| 5.09 | Ethyl | Tetrahydropyran-4-yl | 2-F | 4,00 (m, 2H), 4,10 (t, 2H), 4,27 (t, 2H), 6,80–7,15 (m, 4H) |
| 5.10 | Propyl | Tetrahydropyran-4-yl | 2-F | 76–80 |
| 5.11 | Ethyl | Tetrahydrothiopyran-3-yl | 2-F | 4,10 (t, 2H), 4,27 (t, 2H), 6,80–7,15 (m, 4H), |
| 5.12 | Propyl | Tetrahydrothiopyran-3-yl | 2-F | 4,10 (t, 2H), 4,27 (t, 2H), 6,80–7,15 (m, 4H), |
| 5.13 | Ethyl | Tetrahydropyran-3-yl | 3-F | 3,90 (m, 2H), 4,05 (t, 2H), 4,27 (t, 2H), 6,67 (m, 3H), 7,23 (m, 1H) |
| 5.14 | Propyl | Tetrahydropyran-3-yl | 3-F | 3,90 (m, 2H), 4,05 (t, 2H), 4,27 (t, 2H), 6,67 (m, 3H), 7,23 (m, 1H) |
| 5.15 | Ethyl | Tetrahydropyran-4-yl | 3-F | 3,90–4,10 (m, 4H), 4,27 (t, 2H), 6,67 (m, 3H), 7,23 (m, 1H) |
| 5.16 | Propyl | Tetrahydropyran-4-yl | 3 F | 3,90–4,10 (m, 4H), 4,27 (t, 2H), 6,67 (m, 3H), 7,23 (m, 1H) |
| 5.17 | Ethyl | Tetrahydrothiopyran-3-yl | 3-F | 4,05 (t, 2H), 4,27 (t, 2H), 6,67 (m, 3H) 7,23 (m, 1H) |
| 5.18 | Propyl | Tetrahydrothiopyran-3-yl | 3-F | 4,05 (t, 2H), 4,77 (t, 2H), 6,67 (m, 3H) 7,23 (m, 1H) |
| 5.19 | Ethyl | Tetrahydropyran-3-yl | 4 F | 3,90 (m, 2H), 4,03 (t, 2H), 4,27 (t, 2H), 6,90 (m, 2H), 7,00 (m, 2H) |
| 5.20 | Propyl | Tetrahydropyran-3-yl | 4-F | 3,90 (m, 2H), 4,03 (t, 2H), 4,27 (t, 2H), 6,90 (m, 2H), 7,00 (m, 2H) |
| 5.21 | Ethyl | Tetrahydropyran-4-yl | 4-F | 3,90–4,06 (m, 4H), 4,23 (t, 2H), 6,90 (m, 2H), 7,00 (m, 2H) |
| 5.22 | Propyl | Tetrahydropyran-4-yl | 4-F | 3,90–4,06 (m, 4H), 4,28 (t, 2H), 6,90 (m, 2H), 7,00 (m, 2H) |
| 5.23 | Ethyl | Tetrahydrothiopyran-3-yl | 4-F | 4,03 (t, 2H), 4,27 (t, 2H), 6,90 (m, 2H), 7,00 (m, 2H) |

TABLE 5-continued

Structure: cyclohexane-1,3-dione with OH at position 3, R^f substituent, and 2-position bearing C(R^d)=N-O-CH₂CH₂CH₂-O-phenyl(Radicals)

VI (R^e = —CH₂CH₂—CH₂—O—phenyl-Radicals ; R^g, R^h, R^i = H)

| No. | R^d | R^f | Radicals on phenyl ring | Physical data/¹H-NMR [δ in ppm], mp. [°C.] |
|---|---|---|---|---|
| 5.24 | Propyl | Tetrahydrothiopyran-3-yl | 4-F | 4,03 (t, 2H), 4,27 (t, 2H), 6,90 (m, 2H), 7,00 (m, 2H) |
| 5.25 | Ethyl | Tetrahydropyran-3-yl | 2-Cl | |
| 5.26 | Propyl | Tetrahydropyran-3-yl | 2-Cl | |
| 5.27 | Ethyl | Tetrahydropyran-4-yl | 2-Cl | |
| 5.28 | Propyl | Tetrahydropyran-4-yl | 2-Cl | |
| 5.29 | Ethyl | Tetrahydrothiopyran-3-yl | 2-Cl | |
| 5.30 | Propyl | Tetrahydrothiopyran-3-yl | 2-Cl | |
| 5.31 | Ethyl | Tetrahydropyran-3-yl | 3-Cl | 3,90 (m, 2H), 4,06 (t, 2H), 4,27 (t, 2H), 6,77 (m, 1H), 6,90 (m, 2H), 7,17 (m, 1H) |
| 5.32 | Propyl | Tetrahydropyran-3-yl | 3-Cl | 3,90 (m, 2H), 4,06 (t, 2H), 4,27 (t, 2H), 6,77 (m, 1H), 6,90 (m, 2H), 7,17 (m, 1H) |
| 5.33 | Ethyl | Tetrahydropyran-4-yl | 3-Cl | 3,90–4,10 (m, 4H), 4,27 (t, 2H), 6,77 (m, 1H), 6,90 (m, 2H), 7,17 (m, 1H) |
| 5.34 | Propyl | Tetrahydropyran-4-yl | 3 Cl | 3,90–4,10 (m, 4H), 4,27 (t, 2H), 6,77 (m, 1H), 6,90 (m, 2H), 7,17 (m, 1H) |
| 5.35 | Ethyl | Tetrahydrothiopyran-3-yl | 3-Cl | 4,06 (t, 2H), 4,27 (t, 2H), 6,77 (m, 1H) 6,90 (m, 2H), 7,17 (m, 1H) |
| 5.36 | Propyl | Tetrahydrothiopyran-3-yl | 3-Cl | 4,06 (t, 2H), 4,27 (t, 2H), 6,77 (m, 1H) 6,90 (m, 2H), 7,17 (m, 1H) |
| 5.37 | Ethyl | Tetrahydropyran-3-yl | 4-Cl | 3,90 (m, 2H), 4,03 (t, 2H), 4,23 (t, 2H), 6,80 (m, 2H), 7,20 (m, 2H) |
| 5.38 | Propyl | Tetrahydropyran-3-yl | 4-Cl | 3,90 (m, 2H), 4,03 (t, 2H), 4,23 (t, 2H), 6,80 (m, 2H), 7,20 (m, 2H) |
| 5.39 | Ethyl | Tetrahydropyran-4-yl | 4-Cl | 3,90–4,09 (m, 4H), 4,23 (t, 2H), 6,80 (m, 2H), 7,20 (m, 2H) |
| 5.40 | Propyl | Tetrahydropyran-4-yl | 4-Cl | 3,90–4,09 (m, 4H), 4,23 (t, 2H), 6,80 (m, 2H), 7,20 (m, 2H) |
| 5.41 | Ethyl | Tetrahydrothiopyran-3-yl | 4-Cl | 4,03 (t, 2H), 4,23 (t, 2H), 6,80 (m, 2H), 7,20 (m, 2H) |
| 5.42 | Propyl | Tetrahydrothiopyran-3-yl | 4-Cl | 4,03 (t, 2H), 4,23 (t, 2H), 6,80 (m, 2H), 7,20 (m, 2H) |
| 5.43 | Ethyl | Tetrahydropyran-3-yl | 4-NO₂ | 3,90 (m, 2H), 4,20 (t, 2H), 4,28 (t, 2H), 6,93 (d, 2H), 8,20 (d, H) |
| 5.44 | Propyl | Tetrahydropyran-3-yl | 4-NO₂ | 3,90 (m, 2H), 4,20 (t, 2H), 4,28 (t, 2H), 6,93 (d,2H), 8,20 (d, 2H) |
| 5.45 | Ethyl | Tetrahydropyran-4-yl | 4-NO₂ | 4,00 (m, 2H), 4,20 (t, 2H), 4,28 (t, 2H), 6,93 (d, 2H), 8,20 (d, 2H) |
| 5.46 | Propyl | Tetrahydropyran-4-yl | 4-NO₂ | 4,00 (m, 2H), 4,20 (t, 2H), 4,28 (t, 2H), 6,93 (d, 2H), 8,20 (d, 2H) |
| 5.43 | Ethyl | Tetrahydrothiopyran-3-yl | 4-NO₂ | 4,20 (t, 2H), 4,28 (t, 2H), 6,93 (d, 2H), 8,20 (d, 2H) |
| 5.48 | Propyl | Tetrahydrothiopyran-3-yl | 4-NO₂ | 4,20 (t, 2H), 4,28 (t, 2H), 6,93 (d, 2H), 8,20 (d, 2H) |
| 5.49 | Ethyl | Tetrahydropyran-3-yl | 4-Br | 3,90 (m, 2H), 4,00 (t, 2H), 4,27 (t, 2H), 6,80 (d, 2H), 7,37 (d, 2H) |
| 5.50 | Propyl | Tetrahydropyran-3-yl | 4-Br | 3,90 (m, 2H), 4,00 (t, 2H), 4,27 (t, 2H), 6,80 (d, 2H), 7,37 (d, 2H) |
| 5.51 | Ethyl | Tetrahydropyran-4-yl | 4-Br | 3,90–4,10 (m, 4H), 4,27 (t, 2H), 6,80 (d, 2H), 7,37 (d, 2H) |
| 5.52 | Propyl | Tetrahydropyran-4-yl | 4-Br | 3,90–4,10 (m, 4H), 4,27 (t, 2H), 6,80 (d, 2H), 7,37 (d, 2H) |
| 5.53 | Ethyl | Tetrahydrothiopyran-4-yl | 4-Br | 4,00 (t, 2H), 4,27 (t, 2H), 6,80 (d, 2H), 7,37 (d, 2H) |
| 5.54 | Propyl | Tetrahydrothiopyran-4-yl | 4-Br | 4,00 (t, 2H), 4,27 (t, 2H), 6,80 (d, 2H), 7,37 (d, 2H) |

TABLE 6

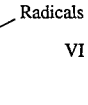

| No. | $R^d$ | $R^f$ | Radicals on phenyl ring | Physical data/$^1$H-NMR [δ in ppm], mp. [°C.] |
|---|---|---|---|---|
| 6.01 | Ethyl | Tetrahydropyran-3-yl | — | 3,90 (m, 2H), 4,17 (t, 2H), 7,10–7,40 (m, 5H) |
| 6.02 | Propyl | Tetrahydropyran-3-yl | — | 3,90 (m, 2H), 4,17 (t, 2H), 7,10–7,40 (m, 5H) |
| 6.03 | Ethyl | Tetrahydropyran-4-yl | — | 4,00 (m, 2H), 4,17 (t, 2H), 7,10–7,40 (m, 5H) |
| 6.04 | Propyl | Tetrahydropyran-4-yl | — | 4,00 (m, 2H), 4,17 (t, 2H), 7,10–7,40 (m, 5H) |
| 6.05 | Ethyl | Tetrahydrothiopyran-3-yl | — | 4,17 (t, 2H), 7,10–7,40 (m, 5H) |
| 6.06 | Propyl | Tetrahydrothiopyran-3-yl | — | 4,17 (t, 2H), 7,10–7,40 (m, 5H) |
| 6.07 | Ethyl | Tetrahydropyran-3-yl | 4-F | 3,90 (m, 2H), 4,17 (t, 2H), 7,00 (t, 2H), 7,33 (m, 2H) |
| 6.08 | Propyl | Tetrahydropyran-3-yl | 4-F | 3,90 (m, 2H), 4,17 (t, 2H), 7,00 (t, 2H), 7,33 (m, 2H) |
| 6.09 | Ethyl | Tetrahydropyran-4-yl | 4-F | 4,00 (m, 2H), 4,17 (t, 2H), 7,00 (t, 2H), 7,33 (m, 2H) |
| 6.10 | Propyl | Tetrahydropyran-4-yl | 4-F | 4,00 (m, 2H), 4,17 (t, 2H), 7,00 (t, 2H), 7,33 (m, 2H) |
| 6.11 | Ethyl | Tetrahydrothiopyran-3-yl | 4-F | 4,17 (t, 2H), 7,00 (t, 2H), 7,33 (m, 2H) |
| 6.12 | Propyl | Tetrahydrothiopyran-3-yl | 4-F | 4,17 (t, 2H), 7,00 (t, 2H), 7,33 (m, 2H) |
| 6.13 | Ethyl | Tetrahydropyran-3-yl | 4-Cl | 3,90 (m, 2H), 4,17 (t, 2H), 7,27 (s, 4H) |
| 6.14 | Propyl | Tetrahydropyran-3-yl | 4-Cl | 3,90 (m, 2H), 4,17 (t, 2H), 7,27 (s, 4H) |
| 6.15 | Ethyl | Tetrahydropyran-4-yl | 4-Cl | 4,00 (m, 2H), 4,17 (t, 2H), 7,27 (s, 4H) |
| 6.16 | Propyl | Tetrahydropyran-4-yl | 4-Cl | 4,00 (m, 2H), 4,17 (t, 2H), 7,27 (s, 4H) |
| 6.17 | Ethyl | Tetrahydrothiopyran-3-yl | 4-Cl | 4,17 (t, 2H), 7,27 (s, 4H) |
| 6.18 | Propyl | Tetrahydrothiopyran-3-yl | 4-Cl | 4,17 (t, 2H), 7,27 (s, 4H) |
| 6.19 | Ethyl | Tetrahydropyran-3-yl | 2-Cl | 3,90 (m, 2H), 4,20 (t, 2H), 7,07–7,40 (m, 4H) |
| 6.20 | Propyl | Tetrahydropyran-3-yl | 2-Cl | 3,90 (m, 2H), 4,20 (t, 2H), 7,07–7,40 (m, 4H) |
| 6.21 | Ethyl | Tetrahydropyran-4-yl | 2-Cl | 4,00 (m, 2H), 4,20 (t, 2H), 7,07–7,40 (m, 4H) |
| 6.22 | Propyl | Tetrahydropyran-4-yl | 2-Cl | 4,00 (m, 2H), 4,20 (t, 2H), 7,07–7,40 (m, 4H) |
| 6.23 | Ethyl | Tetrahydrothiopyran-3-yl | 2-Cl | 4,20 (t, 2H), 7,07–7,40 (m, 4H) |
| 6.24 | Propyl | Tetrahydrothiopyran-3-yl | 2-Cl | 4,20 (t, 2H), 7,07–7,40 (m, 4H) |
| 6.25 | Ethyl | Tetrahydropyran-3-yl | 3-Cl | 3,90 (m, 2H), 4,20 (t, 2H), 7,17 (m, 3H) 7,30 (m, 1H) |
| 6.26 | Propyl | Tetrahydropyran-3-yl | 3-Cl | 3,90 (m, 2H), 4,20 (t, 2H), 7,17 (m, 3H) 7,30 (m, 1H) |
| 6.27 | Ethyl | Tetrahydropyran-4-yl | 3-Cl | 4,00 (m, 2H), 4,20 (t, 2H), 7,17 (m, 3H) 7,30 (m, 1H) |
| 6.28 | Propyl | Tetrahydropyran-4-yl | 3-Cl | 4,00 (m, 2H), 4,20 (t, 2H), 7,17 (m, 3H) 7,30 (m, 1H) |
| 6.29 | Ethyl | Tetrahydrothiopyran-3-yl | 3-Cl | 4,20 (t, 2H), 7,17 (m, 3H), 7,30 (m, 3H) |
| 6.30 | Propyl | Tetrahydrothiopyran-3-yl | 3-Cl | 4,20 (t, 2H), 7,17 (m, 3H), 7,30 (m, 3H) |
| 6.31 | Ethyl | Tetrahydropyran-3-yl | 2,5-Cl$_2$ | 3,90 (m, 2H), 4,20 (t, 2H), 7,07 (dd, 1H), 7,20 (d, 1H) 7,30 (d, 1H) |
| 6.32 | Propyl | Tetrahydropyran-3-yl | 2,5-Cl$_2$ | 3,90 (m, 2H), 4,20 (t, 2H), 7,07 (dd, 1H), 7,20 (d, 1H) 7,30 (d, 1H) |
| 6.33 | Ethyl | Tetrahydropyran-4-yl | 2,5-Cl$_2$ | 4,00 (m, 2H), 4,20 (t, 2H), 7,07 (dd, 1H), 7,20 (d, 1H), 7,30 (d, 1H) |
| 6.34 | Propyl | Tetrahydropyran-4-yl | 2,5-Cl$_2$ | 4,00 (m, 2H), 4,20 (t, 2H), 7,07 (dd, 1H), 7,20 (d, 1H), 7,30 (d, 1H) |
| 6.35 | Ethyl | Tetrahydrothiopyran-3-yl | 2,5-Cl$_2$ | 4,20 (t, 2H), 7,07 (dd, 1H), 7,20 (d, 1H) 7,30 (d, 1H) |
| 6.36 | Propyl | Tetrahydrothiopyran-3-yl | 2,5-Cl$_2$ | 4,20 (t, 2H), 7,07 (dd, 1H), 7,20 (d, 1H) 7,30 (d, 1H) |
| 6.37 | Ethyl | Tetrahydropyran-3-yl | 2,6-Cl$_2$ | 3,90 (m, 2H), 4,20 (t, 2H), 7,20 (t, 1H) 7,40 (d, 2H) |
| 6.38 | Propyl | Tetrahydropyran-3-yl | 2,6-Cl$_2$ | 3,90 (m, 2H), 4,20 (t, 2H), 7,20 (t, 1H) 7,40 (d, 2H) |
| 6.39 | Ethyl | Tetrahydropyran-4-yl | 2,6-Cl$_2$ | 4,00 (m, 2H), 4,20 (t, 2H), 7,20 (t, 1H) 7,40 (d, 2H) |
| 6.40 | Propyl | Tetrahydropyran-4-yl | 2,6-Cl$_2$ | 4,00 (m, 2H), 4,20 (t, 2H), 7,20 (t, 1H) 7,40 (d, 2H) |
| 6.41 | Ethyl | Tetrahydrothiopyran-3-yl | 2,6-Cl$_2$ | 4,20 (t, 2H), 7,20 (t, 1H), 7,40 (d, 2H) |
| 6.42 | Propyl | Tetrahydrothiopyran-3-yl | 2,6-Cl$_2$ | 4,20 (t, 2H), 7,20 (t, 1H), 7,40 (d, 2H) |

TABLE 7

Structure: Cyclohexane-1,3-dione with OH, R^f substituent, and =N-O-CH₂CH₂OCH₂-O-phenyl(Radicals), R^d group. VI (R^e = -CH₂CH₂-O-CH₂-phenyl(Radicals); R^g, R^h, R^i = H)

| No. | R^d | R^f | Radicals on phenyl ring | Physical data/¹H-NMR [δ in ppm], mp. [°C.] |
|---|---|---|---|---|
| 7.01 | Ethyl | Tetrahydropyran-3-yl | — | 3.90 (m, 2H), 4,25 (t, 2H), 4,58 (s, 2H), 7,38 (s, 5H) |
| 7.02 | Propyl | Tetrahydropyran-3-yl | — | 3.90 (m, 2H), 4,25 (t, 2H), 4,58 (s, 2H), 7,38 (s, 5H) |
| 7.03 | Ethyl | Tetrahydropyran-4-yl | — | 4,03 (m, 2H), 4,33 (m, 2H), 4,60 (s, 2H), 7,40 (s, 5H) |
| 7.04 | Propyl | Tetrahydropyran-4-yl | — | 4,03 (m, 2H), 4,33 (m, 2H), 4,60 (s, 2H), 7,40 (s, 5H) |
| 7.05 | Ethyl | Tetrahydrothiopyran-3-yl | — | 4.27 (m, 2H), 4,57 (s, 2H), 7,35 (s, 5H) |
| 7.06 | Propyl | Tetrahydrothiopyran-3-yl | — | 4,27 (m, 2H), 4,57 (s, 2H), 7,35 (s, 5H) |
| 7.07 | Ethyl | Tetrahydropyran-3-yl | 2-F | 3,93 (m, 2H), 4,27 (m, 2H), 4,67 (s, 2H), 6,93–7,50 (m, 4H) |
| 7.08 | Propyl | Tetrahydropyran-3-yl | 2-F | 3,93 (m, 2H), 4,27 (m, 2H), 4,67 (s, 2H), 6,93–7,50 (m, 4H) |
| 7.09 | Ethyl | Tetrahydropyran-4-yl | 2-F | 4,03 (m, 2H), 4,27 (m, 2H), 4,63 (s, 2H), 6,97–7,50 (m,H) |
| 7.10 | Propyl | Tetrahydropyran-4-yl | 2-F | 4,03 (m, 2H), 4,27 (m, 2H), 4,63 (s, 2H) 6,97–7,50 (m, 4H) |
| 7.11 | Ethyl | Tetrahydrothiopyran-3-yl | 2-F | 4,27 (m, 2H), 4,67 (s, 2H), 6,97–7,50 (m, 4H) |
| 7.12 | Propyl | Tetrahydrothiopyran-3-yl | 2-F | 4,27 (m, 2H), 4,67 (s, 2H), 6,97–7,50 (m, 4H) |
| 7.13 | Ethyl | Tetrahydropyran-3-yl | 3-F | 3,93 (m, 2H), 4,27 (m, 2H), 4,57 (s, 2H), 6,90–7,15 (m, 3H), 7,23–7,40 (m, 1H) |
| 7.14 | Propyl | Tetrahydropyran-3-yl | 3-F | 3,93 (m, 2H), 4,27 (m, 2H), 4,57 (s, 2H), 6,90–7,15 (m, 3H), 7,23–7,40 (m, 1H) |
| 7.15 | Ethyl | Tetrahydropyran-4-yl | 3-F | 4,03 (m, 2H), 4,25 (m, 2H), 4,60 (s, 2H), 6,90–7,18 (m, 3H), 7,26–7,40 (m, 1H) |
| 7.16 | Propyl | Tetrahydropyran-4-yl | 3-F | 4,03 (m, 2H), 4,25 (m, 2H), 4,60 (s, 2H), 6,90–7,18 (m, 3H), 7,26–7,40 (m, 1H) |
| 7.17 | Ethyl | Tetrahydrothiopyran-3-yl | 3-F | 4,27 (m, 2H), 4,60 (s, 2H), 6.90–7,15 (m, 3H), 7,23–7,40 (m, 1H) |
| 7.18 | Propyl | Tetrahydrothiopyran-3-yl | 3-F | 4,27 (m, 2H), 4,60 (s, 2H), 6,90–7,15 (m, 3H), 7,23–7,40 (m, 1H) |
| 7.19 | Ethyl | Tetrahydropyran-3-yl | 4-F | 3,93 (m, 2H), 4,23 (m, 2H), 4,53 (s, 2H), 7,00 (m, 2H), 7,30 (m, 2H) |
| 7.20 | Propyl | Tetrahydropyran-3-yl | 4-F | 3,93 (m, 2H), 4,23 (m, 2H), 4,53 (s, 2H), 7,00 (m, 2H), 7,30 (m, 2H) |
| 7.21 | Ethyl | Tetrahydropyran-4-yl | 4-F | 92 |
| 7.22 | Propyl | Tetrahydropyran-4-yl | 4-F | 4,00 (m, 2H), 4,23 (m, 2H) 4,53 (s, 2H), 7,03 (m, 2H), 7,30 (m, 2H) |
| 7.23 | Ethyl | Tetrahydrothiopyran-3-yl | 4-F | 4,27 (m, 2H), 4,53 (s, 2H), 7,03 (m, 2H), 7,30 (m, 2H) |
| 7.24 | Propyl | Tetrahydrothiopyran-3-yl | 4-F | 4,27 (m, 2H), 4,53 (s, 2H), 7,03 (m, 2H), 7,30 (m, 2H) |
| 7.25 | Ethyl | Tetrahydropyran-3-yl | 2-Cl | |
| 7.26 | Propyl | Tetrahydropyran-3-yl | 2-Cl | |
| 7.27 | Ethyl | Tetrahydropyran-4-yl | 2-Cl | |
| 7.28 | Propyl | Tetrahydropyran-4-yl | 2-Cl | |
| 7.29 | Ethyl | Tetrahydrothiopyran-3-yl | 2-Cl | |
| 7.30 | Propyl | Tetrahydrothiopyran-3-yl | 2-Cl | |
| 7.31 | Ethyl | Tetrahydropyran-3-yl | 3-Cl | |
| 7.32 | Propyl | Tetrahydropyran-3-yl | 3-Cl | |
| 7.33 | Ethyl | Tetrahydropyran-4-yl | 3-Cl | |
| 7.34 | Propyl | Tetrahydropyran-4-yl | 3-Cl | |
| 7.35 | Ethyl | Tetrahydrothiopyran-3-yl | 3-Cl | |
| 7.36 | Propyl | Tetrahydrothiopyran-3-yl | 3-Cl | |
| 7.37 | Ethyl | Tetrahydropyran-3-yl | 4-Cl | 3,93 (m, 2H), 4,27 (m, 2H), 4,53 (s, 2H), 7,28 (m, 4H) |
| 7.38 | Propyl | Tetrahydropyran-3-yl | 4-Cl | 3,93 (m, 2H), 4,27 (m, 2H), 4,53 (s, 2H) 7,28 (m, 4H) |
| 7.39 | Ethyl | Tetrahydropyran-4-yl | 4-Cl | 67–72 |
| 7.40 | Propyl | Tetrahydropyran-4-yl | 4-Cl | 4,00 (m, 2H), 4,23 (m, 2H), 4,53 (s, 2H), 7,28 (m, 4H) |
| 7.41 | Ethyl | Tetrahydrothiopyran-3-yl | 4-Cl | 4,27 (m, 2H), 4,53 (s, 2H), 7,28 (m, 4H) |
| 7.42 | Propyl | Tetrahydrothiopyran-3-yl | 4-Cl | 4,27 (m, 2H), 4,53 (s, 2H), 7,28 (m, 4H) |
| 7.43 | Ethyl | Tetrahydropyran-3-yl | 2-CH₃ | 3,93 (m, 2H), 4,23 (m, 2H), 4,57 (s, 2H), |

TABLE 7-continued

Structure: cyclohexane-dione with OH, R^f, NO—CH₂CH₂OCH₂—O—phenyl(Radicals), R^d; VI (R^e = —CH₂CH₂—O—CH₂—phenyl(Radicals); R^g, R^h, R^i = H)

| No. | R^d | R^f | Radicals on phenyl ring | Physical data/$^1$H-NMR [δ in ppm], mp. [°C.] |
|---|---|---|---|---|
| 7.44 | Propyl | Tetrahydropyran-3-yl | 2-CH₃ | 3,93 (m, 2H), 4,23 (m, 2H), 4,57 (s, 2H), 7,09–7,33 (m, 4H) |
| 7.45 | Ethyl | Tetrahydropyran-4-yl | 2-CH₃ | 4,00 (m, 2H), 4,23 (m, 2H) 4,57 (s, 2H) 7,09–7,33 (m, 4H) |
| 7.46 | Propyl | Tetrahydropyran-4-yl | 2-CH₃ | 4,00 (m, 2H), 4,23 (m, 2H), 4,57 (s, 2H), 7,09–7,33 (m, 4H) |
| 7.47 | Ethyl | Tetrahydrothiopyran-3-yl | 2-CH₃ | 4,23 (m, 2H), 4,57 (s, 2H), 7,09–7,33 (m, 4H) |
| 7.48 | Propyl | Tetrahydrothiopyran-3-yl | 2-CH₃ | 4,23 (m, 2H), 4,57 (s, 2H), 7,09–7,33 (m, 4H) |
| 7.49 | Ethyl | Tetrahydropyran-3-yl | 3-CH₃ | 3,93 (m, 2H), 4,25 (m, 2H), 4,57 (s, 2H), 7,00–7,32 (m, 4H) |
| 7.50 | Propyl | Tetrahydropyran-3-yl | 3-CH₃ | 3,93 (m, 2H), 4,25 (m, 2H), 4,57 (s, 2H), 7,00–7,32 (m, 4H) |
| 7.51 | Ethyl | Tetrahydropyran-4-yl | 3-CH₃ | 4,00 (m, 2H), 4,27 (m, 2H), 4,57 (s, 2H), 7,00–7,32 (m, 4H) |
| 7.52 | Propyl | Tetrahydropyran-4-yl | 3-CH₃ | 4,00 (m, 2H), 4,27 (m, 2H), 4,57 (s, 2H), 7,00–7,32 (m, 4H) |
| 7.53 | Ethyl | Tetrahydrothiopyran-3-yl | 3-CH₃ | 4,27 (m, 2H), 4,60 (s, 2H), 7,00–7,32 (m, 4H) |
| 7.54 | Propyl | Tetrahydrothiopyran-3-yl | 3-CH₃ | 4,27 (m, 2H), 4,60 (s, 2H), 7,00–7,32 (m, 4H) |
| 7.55 | Ethyl | Tetrahydropyran-3-yl | 4-CH₃ | 3,93 (m, 2H), 4,20 (m, 2H), 4,53 (s, 2H), 7,07–7,30 (m, 4H) |
| 7.56 | Propyl | Tetrahydropyran-3-yl | 4-CH₃ | 3,93 (m, 2H), 4,20 (m, 2H), 4,53 (s, 2H), 7,07–7,30 (m, 4H) |
| 7.57 | Ethyl | Tetrahydropyran-4-yl | 4-CH₃ | 4,00 (m, 2H), 4,23 (m, 2H), 4,57 (s, 2H), 7,03-7,27 (m, 4H) |
| 7.58 | Propyl | Tetrahydropyran-4-yl | 4-CH₃ | 4,00 (m, 2H), 4,23 (m, 2H), 4,57 (s, 2H), 7,03–7,27 (m, 4H) |
| 7.59 | Ethyl | Tetrahydrothiopyran-3-yl | 4-CH₃ | 4,23 (m, 2H), 4,57 (s, 2H), 7,07–7,30 (m, 4H) |
| 7.60 | Propyl | Tetrahydrothiopyran-3-yl | 4-CH₃ | 4,28 (m, 2H), 4,57 (s, 2H), 7,07–7,30 (m, 4H) |
| 7.61 | Ethyl | Tetrahydropyran-3-yl | 4-tert.-C₄H₉ | 3,93 (m, 2H), 4,23 (m, 2H), 4,53 (s, 2H), 7,20–7,40 (m, 4H) |
| 7.62 | Propyl | Tetrahydropyran-3-yl | 4-tert.-C₄H₉ | 3,93 (m, 2H), 4,23 (m, 2H), 4,53 (s, 2H), 7,20–7,40 (m, 4H) |
| 7.63 | Ethyl | Tetrahydropyran-4-yl | 4-tert.-C₄H₉ | 4,00 (m, 2H), 4,23 (m, 2H), 4,53 (s, 2H), 7,20–7,40 (m, 4H) |
| 7.64 | Propyl | Tetrahydropyran-4-yl | 4-tert.-C₄H₉ | 4,00 (m, 2H), 4,23 (m, 2H), 4,53 (s, 2H), 7,20–7,40 (m, 4H) |
| 7.65 | Ethyl | Tetrahydrothiopyran-3-yl | 4-tert.-C₄H₉ | 4,23 (m, 2H), 4,53 (s, 2H), 7,20–7,40 (m, 4H) |
| 7.66 | Propyl | Tetrahydrothiopyran-3-yl | 4-tert.-C₄H₉ | 4,23 (m, 2H), 4,53 (s, 2H), 7,20–7,40 (m, 4H) |

TABLE 8

Structure: cyclohexane-dione with OH, R^f, NO—CH₂CH₂SCH₂—phenyl(Radicals), R^d; VI (R^e = —CH₂CH₂—S—CH₂—phenyl(Radicals); R^g, R^h, R^i = H)

| No. | R^d | R^f | Radicals on phenyl ring | Physical data/$^1$H-NMR [δ in ppm], mp. [°C.] |
|---|---|---|---|---|
| 8.01 | Ethyl | Tetrahydropyran-3-yl | — | 3,73 (s, 2H), 3,90 (m, 2H), 4,17 (t, 2H), 7,28 (s, 5H) |
| 8.02 | Propyl | Tetrahydropyran-3-yl | — | 3,73 (s, 2H), 3,90 (m, 2H), 4,17 (t, 2H), 7,28 (s, 5H) |
| 8.03 | Ethyl | Tetrahydropyran-4-yl | — | 3,77 (s, 2H), 4,00 (m, 2H), 4,13 (t, 2H), 7,28 (s, 5H) |

TABLE 8-continued structure: cyclohexanedione with OH, R^f substituent, =N-O-CH₂CH₂SCH₂-phenyl(Radicals), R^d group; VI (R^e = —CH₂CH₂—S—CH₂—phenyl(Radicals); R^g, R^h, R^i = H)

| No. | R^d | R^f | Radicals on phenyl ring | Physical data/$^1$H-NMR [δ in ppm], mp. [°C.] |
|---|---|---|---|---|
| 8.04 | Propyl | Tetrahydropyran-4-yl | — | 3,77 (s, 2H), 4,00 (m, 2H), 4,13 (t, 2H), 7,28 (s, 5H) |
| 8.05 | Ethyl | Tetrahydrothiopyran-3-yl | — | 3,80 (s, 2H), 4,13 (t, 2H), 7,28 (s, 5H) |
| 8.06 | Propyl | Tetrahydrothiopyran-3-yl | — | 3,80 (s, 2H), 4,13 (t, 2H), 7,28 (s, 5H) |
| 8.07 | Ethyl | Tetrahydropyran-3-yl | 4-F | 3,72 (s, 2H), 3,90 (m, 2H), 4,13 (t, 2H), 7,00 (m, 2H), 7,30 (m, 2H) |
| 8.08 | Propyl | Tetrahydropyran-3-yl | 4-F | 3,72 (s, 2H), 3,90 (m, 2H), 4,13 (t, 2H), 7,00 (m, 2H), 7,30 (m, 2H) |
| 8.09 | Ethyl | Tetrahydropyran-4-yl | 4-F | 63–65 |
| 8.10 | Propyl | Tetrahydropyran-4-yl | 4-F | 3,73 (s, 2H), 4,00 (m, 2H), 4,13 (t, 2H), 7,00 (m, 2H), 7,30 (m, 2H) |
| 8.11 | Ethyl | Tetrahydrothiopyran-3-yl | 4-F | 3,75 (s, 2H), 4,13 (t, 2H), 7,00 (m, 2H), 7,30 (m, 2H) |
| 8.12 | Propyl | Tetrdhydropyran-3-yl | 4-F | 3,75 (s, 2H), 4,13 (t, 2H), 7,00 (m, 2H), 7,30 (m, 2H) |
| 8.13 | Ethyl | Tetrahydropyran-3-yl | 4-Cl | 3,77 (s, 2H), 3,93 (m, 2H), 4,13 (t, 2H), 7,30 (s, 4H) |
| 8.14 | Propyl | Tetrahydropyran-3-yl | 4-Cl | 3,77 (s, 2H), 3,93 (m, 2H), 4,13 (t, 2H), 7,30 (s, 4H) |
| 8.15 | Ethyl | Tetrahydropyran-4-yl | 4-Cl | 3,73 (s, 2H), 4,00 (m, 2H), 4,17 (t, 2H), 7,30 (s, 4H) |
| 8.16 | Propyl | Tetrahydropyran-4-yl | 4-Cl | 3,73 (s, 2H), 4,00 (m, 2H), 4,17 (t, 2H), 7,30 (s, 4H) |
| 8.17 | Ethyl | Tetrahydrothiopyran-3-yl | 4-Cl | 3,73 (s, 2H) 4,13 (m, 2H), 7,30 (s, 4H) |
| 8.18 | Propyl | Tetrahydrothiopyran-3-yl | 4-Cl | 3,73 (s, 2H) 4,13 (m, 2H), 7,30 (s, 4H) |

TABLE 9 structure: cyclohexanedione with OH, R^f substituent, =N-O-CH₂CH₂CH₂CH₂-O-phenyl(Radicals), R^d group; VI (R^e = —CH₂CH₂CH₂CH₂—O—phenyl(Radicals); R^g, R^h, R^i = H)

| No. | R^d | R^f | Radicals on phenyl ring | Physical data/$^1$H-NMR [δ in ppm], mp. [°C.] |
|---|---|---|---|---|
| 9.01 | Ethyl | Tetrahydropyran-3-yl | — | 3,70–4,20 (m, 6H), 6,90 (m, 3H), 7,30 (m, 2H) |
| 9.02 | Propyl | Tetrahydropyran-3-yl | — | 3,70–4,20 (m, 6H), 6,90 (m, 3H), 7,30 (m, 2H) |
| 9.03 | Ethyl | Tetrahydropyran-4-yl | — | 3,83–4,23 (m, 6H), 6,90 (m, 3H), 7,30 (m, 2H) |
| 9.04 | Propyl | Tetrahydropyran-4-yl | — | 3,83–4,23 (m, 6H), 6,90 (m, 3H), 7,30 (m, 2H) |
| 9.05 | Ethyl | Tetrahydrothiopyran-3-yl | — | 4,00 (bs, 2H), 4,13 (bs, 2H), 6,90 (m, 3H) 7,30 (m, 2H) |
| 9.06 | Propyl | Tetrahydrothiopyran-3-yl | — | 4,00 (bs, 2H), 4,13 (bs, 2H), 6,90 (m, 3H) 7,30 (m, 2H) |
| 9.07 | Ethyl | Tetrahydropyran-3-yl | 2-F | 3,93 (m, 2H), 4,00–4,20 (m, 4H), 6,80–7,15 (m, 4H) |
| 9.08 | Propyl | Tetrahydropyran-3-yl | 2-F | 3,93 (m, 2H), 4,00–4,20 (m, 4H), 6,80–7,15 (m, 4H) |
| 9.09 | Ethyl | Tetrahydropyran-4-yl | 2-F | 68–72 |
| 9.10 | Propyl | Tetrahydropyran-4-yl | 2-F | 3,90–4,20 (m, 6H), 6,80–7,15 (m, 4H) |
| 9.11 | Ethyl | Tetrahydrothiopyran-3-yl | 2-F | 4,00–4,20 (m, 4H), 6,80–7,15 (m, 4H) |
| 9.12 | Propyl | Tetrahydrothiopyran-3-yl | 2-F | 4,00–4,20 (m, 4H), 6,80–7,15 (m, 4H) |
| 9.13 | Ethyl | Tetrahydropyran-3-yl | 3-F | |
| 9.14 | Propyl | Tetrahydropyran-3-yl | 3-F | |
| 9.15 | Ethyl | Tetrahydropyran-4-yl | 3-F | |
| 9.16 | Propyl | Tetrahydropyran-4-yl | 3-F | |
| 9.17 | Ethyl | Tetrahydrothiopyran-3-yl | 3-F | |
| 9.18 | Propyl | Tetrahydrothiopyran-3-yl | 3-F | |
| 9.19 | Ethyl | Tetrahydropyran-3-yl | 4-F | 3,80–4,20 (m, 6H), 6,75–7,05 (m, 4H) |
| 9.20 | Propyl | Tetrahydropyran-3-yl | 4-F | 3,80–4,20 (m, 6H), 6,75–7,05 (m, 4H) |

TABLE 9-continued

| No. | $R^d$ | $R^f$ | Radicals on phenyl ring | Physical data/$^1$H-NMR [δ in ppm], mp. [°C.] |
|---|---|---|---|---|
| 9.21 | Ethyl | Tetrahydropyran-4-yl | 4-F | 3,90–4,20 (m, 6H), 6,75–7,05 (m, 4H) |
| 9.22 | Propyl | Tetrahydropyran-4-yl | 4-F | 3,90–4,20 (m, 6H), 6,75–7,05 (m, 4H) |
| 9.23 | Ethyl | Tetrahydrothiopyran-3-yl | 4-F | 3,90–4,20 (m, 4H), 6,75–7,05 (m, 4H) |
| 9.24 | Propyl | Tetrahydrothiopyran-3-yl | 4-F | 3,90–4,20 (m, 4H), 6,75–7,05 (m, 4H) |
| 9.25 | Ethyl | Tetrahydropyran-3-yl | 4-Cl | 3,80–4,20 (m, 6H), 6,80 (m, 2H), 7,20 (m, 2H) |
| 9.26 | Propyl | Tetrahydropyran-3-yl | 4-Cl | 3,80–4,20 (m, 6H), 6,80 (m, 2H), 7,20 (m, 2H) |
| 9.27 | Ethyl | Tetrahydropyran-4-yl | 4-Cl | 3,90–4,20 (m, 6H), 6,80 (m, 2H), 7,20 (m, 2H) |
| 9.28 | Propyl | Tetrahydropyran-4-yl | 4-Cl | 3,90–4,20 (m, 6H), 6,80 (m, 2H), 7,20 (m, 2H) |
| 9.29 | Ethyl | Tetrahydrothiopyran-3-yl | 4-Cl | 3,90–4,20 (m, 4H), 6,80 (m, 2H), 7,20 (m, 2H) |
| 9.30 | Propyl | Tetrahydrothiopyran-3-yl | 4-Cl | 3,90–4,20 (m, 4H), 6,80 (m, 2H), 7,20 (m, 2H) |
| 9.31 | Ethyl | Tetrahydropyran-3-yl | 2,6-Cl$_2$ | 3,93 (m, 2H), 4,00–4,25 (m, 4H), 7,00 (t, 1H), 7,30 (d, 2H) |
| 9.32 | Propyl | Tetrahydropyran-3-yl | 2,6-Cl$_2$ | 3,93 (m, 2H), 4,00–4,25 (m, 4H), 7,00 (t, 1H), 7,30 (d, 2H) |
| 9.33 | Ethyl | Tetrahydropyran 4-yl | 2,6-Cl$_2$ | 3,90–4,25 (m, 6H), 7,00 (t, 1H), 7,30 (d, 2H) |
| 9.34 | Propyl | Tetrahydropyran-4-yl | 2,6-Cl$_2$ | 3,90–4,25 (m, 6H), 7,00 (t, 1H), 7,30 (d, 2H) |
| 9.35 | Ethyl | Tetrahydrothiopyran-3-yl | 2,6-Cl$_2$ | 4,00–4,20 (m, 4H), 7,00 (t, 1H), 7,30 (d, 2H) |
| 9.36 | Propyl | Tetrahydrothiopyran-3-yl | 2,6-Cl$_2$ | 4,00–4,20 (m, 4H), 7,00 (t, 1H), 7,30 (d, 2H) |

TABLE 10

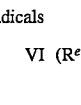

| No. | $R^d$ | $R^f$ | Radicals on phenyl ring | Physical data/$^1$H-NMR [δ in ppm], mp. [°C.] |
|---|---|---|---|---|
| 10.01 | Ethyl | Tetrahydropyran-3-yl | — | 3,90 (m, 2H), 4,20 (m, 2H), 7,25 (m, 5H) |
| 10.02 | Propyl | Tetrdhydropyran-3-yl | — | 3,90 (m, 2H), 4,20 (m, 2H), 7,25 (m, 5H) |
| 10.03 | Ethyl | Tetrahydropyran-4-yl | — | |
| 10.04 | Propyl | Tetrahydropyran-4-yl | — | |
| 10.05 | Ethyl | Tetrahydrothiopyran-3-yl | — | 4,20 (m, 2H), 7,25 (m, 5H) |
| 10.06 | Propyl | Tetrahydrothiopyran-3-yl | — | 4,20 (m, 2H), 7,25 (m, 5H) |
| 10.07 | Ethyl | Tetrahydropyran-3-yl | 4-F | 3,90 (m, 2H), 4,17 (m, 2H), 6,93 (m, 2H), 7,13 (m, 2H) |
| 10.08 | Propyl | Tetrahydropyran-3-yl | 4-F | 3,90 (m, 2H), 4,17 (m, 2H), 6,93 (m, 2H), 7,13 (m, 2H) |
| 10.09 | Ethyl | Tetrahydropyran-4-yl | 4-F | |
| 10.10 | Propyl | Tetrahydropyran-4-yl | 4-F | |
| 10.11 | Ethyl | Tetrahydrothiopyran-3-yl | 4-F | 4,17 (m, 2H), 6,93 (m, 2H), 7,13 (m, 2H) |
| 10.12 | Propyl | Tetrahydrothiopyran-3-yl | 4-F | 4,17 (m, 2H), 6,93 (m, 2H), 7,13 (m, 2H) |
| 10.13 | Ethyl | Tetrahydropyran-3-yl | 4-Cl | 3,90 (m, 2H), 4,17 (m, 2H), 7,13 (m, 4H) |
| 10.14 | Propyl | Tetrahydropyran-3-yl | 4-Cl | 3,90 (m, 2H), 4,17 (m, 2H), 7,13 (m, 4H) |
| 10.15 | Ethyl | Tetrahydropyran-4-yl | 4-Cl | |
| 10.16 | Propyl | Tetrahydropyran-4-yl | 4-Cl | |
| 10.17 | Ethyl | Tetrahydrothiopyran-3-yl | 4-Cl | 4,17 (m, 2H), 7,13 (m, 4H) |
| 10.18 | Propyl | Tetrahydrothiopyran-3-yl | 4-Cl | 4,17 (m, 2H), 7,13 (m, 4H) |

TABLE 11

| No. | R$^d$ | R$^f$ | Radicals on phenyl ring | Physical data/$^1$H-NMR [δ in ppm], mp. [°C.] |
|---|---|---|---|---|
| 11.01 | Ethyl | Tetrahydropyran-3-yl | — | 3,80–4,17 (m, 6H), 6,90 (m, 3H), 7,27 (m, 2H) |
| 11.02 | Propyl | Tetrahydropyran-3-yl | — | 3,80–4,17 (m, 6H), 6,90 (m, 3H), 7,27 (m, 2H) |
| 11.03 | Ethyl | Tetrahydropyran-4-yl | — | 3,90–4,17 (m, 6H), 6,90 (m, 3H), 7,27 (m, 2H) |
| 11.04 | Propyl | Tetrahydropyran-4-yl | — | 3,90–4,17 (m, 6H), 6,90 (m, 3H), 7,27 (m, 2H) |
| 11.05 | Ethyl | Tetrahydrothiopyran-3-yl | — | 3,97 (t, 2H), 4,07 (t, 2H), 6,90 (m, 3H), 7,27 (m, 2H) |
| 11.06 | Propyl | Tetrahydrothiopyran-3-yl | — | 3,97 (t, 2H), 4,07 (t, 2H), 6,90 (m, 3H), 7,27 (m, 2H) |
| 11.07 | Ethyl | Tetrahydropyran-3-yl | 4-F | 3,90 (m, 4H), 4,03 (t, 2H), 6,70–7,03 (m, 4H) |
| 11.08 | Propyl | Tetrahydropyran-3-yl | 4-F | 3,90 (m, 4H), 4,03 (t, 2H), 6,70–7,03 (m, 4H) |
| 11.09 | Ethyl | Tetrahydropyran-4-yl | 4-F | 3,83–4,13 (m, 6H), 6,70–7,03 (m, 4H) |
| 11.10 | Propyl | Tetrahydropyran-4-yl | 4-F | 3,83–4,13 (m, 6H), 6,70–7,03 (m, 4H) |
| 11.11 | Ethyl | Tetrahydrothiopyran-3-yl | 4-F | 3,90 (t, 2H), 4,03 (t, 2H) 6,70–7,03 (m, 4H) |
| 11.12 | Propyl | Tetrahydrothiopyran-3-yl | 4-F | 3,90 (t, 2H), 4,03 (t, 2H) 6,70–7,03 (m, 4H) |
| 11.13 | Ethyl | Tetrahydropyran-3-yl | 4-Cl | 3,80–4,10 (m, 6H), 6,80 (d, 2H), 7,20 (d, 2H) |
| 11.14 | Propyl | Tetrahydropyran-3-yl | 4-Cl | 3,80–4,10 (m, 6H), 6,80 (d, 2H), 7,20 (d, 2H) |
| 11.15 | Ethyl | Tetrahydropyran-4-yl | 4-Cl | 3,87–4,10 (m, 6H), 6,80 (d, 2H), 7,20 (d, 2H) |
| 11.16 | Propyl | Tetrdhydropyran-4-yl | 4-Cl | 3,87–4,10 (m, 6H), 6,80 (d, 2H), 7,20 (d, 2H) |
| 11.17 | Ethyl | Tetrahydrothiopyran-3-yl | 4-Cl | 54–61 |
| 11.18 | Propyl | Tetrahydrothiopyran-3-yl | 4-Cl | 3,90 (t, 2H), 4,07 (t, 2H), 6,80 (d, 2H) 7,20 (d, 2H) |

TABLE 12

| No. | R$^d$ | R$^e$ | R$^f$ | R$^g$ | R$^h$ | R$^i$ | Reference |
|---|---|---|---|---|---|---|---|
| 12.1 | C$_3$H$_7$ | CH$_2$CH=CH$_2$ | CH$_3$ | CH$_3$ | CO$_2$CH$_3$ | Na | DE-A 2 439 104 |
| 12.2 | C$_3$H$_7$ | CH$_2$CH$_3$ | CH$_2$CH(CH$_3$)SCH$_2$CH$_3$ | H | H | H | DE-A 2 822 304 |
| 12.3 | C$_2$H$_5$ | CH$_2$CH=CHCl | CH$_2$CH(CH$_3$)SCH$_2$CH$_3$ | H | H | H | US-A 4 440 566 |
| 12.4 | C$_3$H$_7$ | CH$_2$CH=CHCl | CH$_2$CH(CH$_3$)SCH$_2$CH$_3$ | H | H | H | US-A 4 440 566 |
| 12.5 | C$_3$H$_7$ | C$_2$H$_5$ | (tetrahydrothiopyranyl) | H | H | H | EP-A 71 707 |
| 12.6 | C$_2$H$_5$ | C$_2$H$_5$ | (tetrahydrothiopyranyl) | H | H | H | EP-A 71 707 |
| 12.7 | CH$_3$ | CH$_2$CH=CHCH$_3$ | (tetrahydrothiopyranyl) | H | H | H | EP-A 71 707 |
| 12.8 | C$_3$H$_7$ | C$_2$H$_5$ | (tetrahydropyranyl) | H | H | H | EP-A 71 707 |

TABLE 12-continued
| No. | $R^d$ | $R^e$ | $R^f$ | $R^g$ | $R^h$ | $R^i$ | Reference |
|---|---|---|---|---|---|---|---|
| 12.9 | $C_2H_5$ | $CH_2CH=CHCl$ | 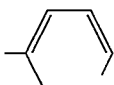 | H | H | H | EP-A 142 741 |
| 12.10 | $C_3H_7$ | $C_2H_5$ | 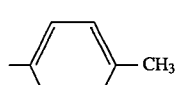 | H | H | H | EP-A 66 195 |
| 12.11 | $C_2H_5$ | $C_2H_5$ | 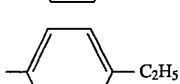 | H | H | H | DE-A 24 39 104 |
| 12.12 | $C_2H_5$ | $CH_2CH=CHCH_3$ | 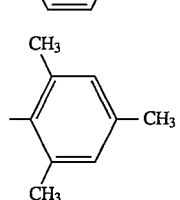 | H | H | H | DE-A 38 08 072 |
| 12.13 | $C_2H_5$ | $C_2H_5$ | 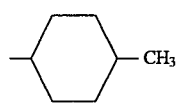 | H | H | H | EP-A 880 301 |
| 12.14 | $C_3H_7$ | $CH_2CH=CHCl$ | 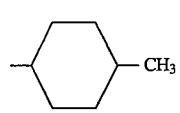 | H | H | H | EP-A 88 299 |
| 12.15 | $C_3H_7$ | $CH_2CH=CHCH_3$ | 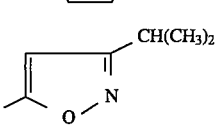 | H | H | H | EP-A 88 299 |
| 12.16 | $C_2H_5$ | $CH_2CH=CHCH_3$ | 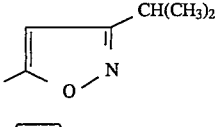 | H | H | H | EP-A 238 021 |
| 12.17 | $C_3H_7$ | $CH_2CH=CHCH_3$ | 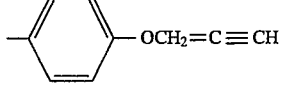 | H | H | H | EP-A 238 021 |
| 12.18 | $C_2H_5$ | $CH_2CH=CHCl$ | 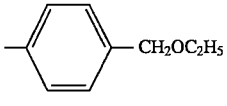 | H | H | H | EP-A 137 174 |
| 12.19 | $C_3H_7$ | $C_2H_5$ |  | H | H | H | EP-A 2 137 200 |

TABLE 12-continued $$\text{VI}$$

Structure: cyclohexenone with $OR^i$, $R^f$, $R^g$, $R^h$ substituents, and side chain C(=NOR^e)R^d

| No. | $R^d$ | $R^e$ | $R^f$ | $R^g$ | $R^h$ | $R^i$ | Reference |
|---|---|---|---|---|---|---|---|
| 12.20 | $C_3H_7$ | $C_2H_5$ | 3,4-dibromo-tetrahydropyran-3-yl (Br at 3, Br at 4) | H | H | H | EP-A 230 235 |
| 12.21 | $C_3H_7$ | $CH_2CH=CHCl$ | 3,4-dibromo-tetrahydropyran-3-yl | H | H | H | EP-A 230 235 |
| 12.22 | $C_3H_7$ | $CH_2CH=CHCl$ | 2,6,6-trimethylcyclohex-1-enyl | H | H | H | EP-A 46 860 |
| 12.23 | $C_3H_7$ | $C_2H_5$ | cyclohexyl | H | H | H | JP-A 540 191 945 |
| 12.24 | $C_3H_7$ | $C_2H_5$ | cyclohex-1-enyl | H | H | H | EP-A 46 860 |
| 12.25 | $CH_3$ | $CH_2CH=CHCl$ | 4-methylcyclohexyl | H | H | H | EP-A 88 299 |
| 12.26 | $C_3H_7$ | $C_2H_5$ | 4-(trifluoromethyl)phenyl | H | H | K | EP-A 137 174 |
| 12.27 | $C_2H_5$ | $CH_2CH=CHCl$ | 2,6,6-trimethylcyclohex-1-enyl | H | H | H | EP-A 46 860 |
| 12.28 | $C_3H_7$ | $CH_2CH=CHCH_3$ | 2-methyl-1,3-thiazol-4-yl | H | H | H | EP-A 125 094 |
| 12.29 | $C_3H_7$ | $CH_2CH=CHCl$ | 2-methyl-1,3-thiazol-4-yl | H | H | H | EP-A 125 094 |

TABLE 12-continued
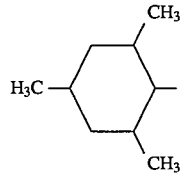
| No. | $R^d$ | $R^e$ | $R^f$ | $R^g$ | $R^h$ | $R^i$ | Reference |
|---|---|---|---|---|---|---|---|
| 12.30 | $C_3H_7$ | $C_2H_5$ | 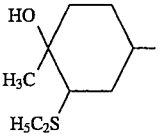 | H | H | H | EP-A 88 299 |
| 12.31 | $C_3H_7$ | $CH_2CH=CH_2$ | 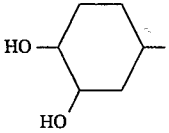 | H | H | H | EP-A 228 598 |
| 12.32 | $C_2H_5$ | $C_2H_5$ | 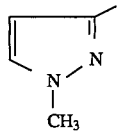 | H | H | H | EP-A 228 598 |
| 12.33 | $C_3H_7$ | $C_2H_5$ | 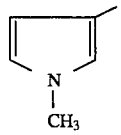 | H | H | H | EP-A 66 195 |
| 12.34 | $C_3H_7$ | $CH_2CH=CHCl$ | 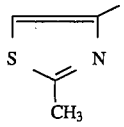 | H | H | H | EP-A 66195 |
| 12.35 | $C_3H_7$ | $CH_2CH=CH_2$ | 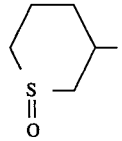 | H | H | H | EP-A 125 094 |
| 12.36 | $C_3H_7$ | $C_3H_7$ | $CH(SCH_2CH_3)_2$ | H | H | H | EP-A 230 260 |
| 12.37 | $C_3H_7$ | $C_2H_5$ | 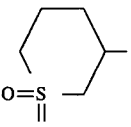 | H | H | H | EP-A 115 808 |
| 12.38 | $C_3H_7$ | $C_2H_5$ |  | H | H | H | EP-A 115 808 |
| 12.39 | $C_3H_7$ | $C_2H_5$ | $CH_3$ | $CH_3$ | $C(CH_3)=NOCH_3$ | H | EP-A 172 551 |

TABLE 12-continued

Structure VI:

Cyclohexanone core with substituents: OR^i (vinyl position), =NOR^e with R^d group, R^f, R^g, R^h on the ring.

| No. | R^d | R^e | R^f | R^g | R^h | R^i | Reference |
|---|---|---|---|---|---|---|---|
| 12.40 | C$_3$H$_7$ | CH$_2$CH=CH$_2$ | tetrahydrothiopyranyl-S,S-dioxide | OH | H | H | Proceedings Brit. Crop-Protection Conference - weeds 1985 Vol. 1 page 93–98 |
| 12.41 | C$_2$H$_5$ | CH$_2$CH=CH—C$_6$H$_4$—Cl | tetrahydrothiopyranyl | H | H | H | EP-A 38 38 309 |
| 12.42 | C$_2$H$_5$ | CH$_2$CH$_2$—CH=CH—C$_6$H$_4$—Cl | tetrahydrothiopyranyl | H | H | H | EP-A 38 38 309 |
| 12.43 | C$_2$H$_5$ | CH$_2$CH$_2$—CH=CH—C$_6$H$_4$—F | tetrahydrothiopyranyl | H | H | H | EP-A 38 38 309 |
| 12.44 | n-C$_3$H$_7$ | CH$_2$CH$_2$—CH=CH—C$_6$H$_4$—F | tetrahydrothiopyranyl | H | H | H | EP-A 38 38 309 |
| 12.45 | C$_2$H$_5$ | CH$_2$CH=CH—CH$_2$—C$_6$H$_5$ | tetrahydrothiopyranyl | H | H | H | EP-A 38 38 309 |
| 12.46 | n-C$_3$H$_7$ | CH$_2$-(2-chloro-thien-5-yl) | tetrahydrothiopyranyl | H | H | H | EP-A 177 913 |
| 12.47 | C$_2$H$_5$ | CH$_2$-(2-chloro-thien-5-yl) | tetrahydrothiopyranyl | H | H | H | EP-A 177 913 |
| 12.48 | C$_2$H$_5$ | CH$_2$-(2-chloro-thien-5-yl) | tetrahydropyranyl | H | H | H | EP-A 177 913 |
| 12.49 | n-C$_3$H$_7$ | CH$_2$-(2-chloro-thien-5-yl) | tetrahydropyranyl | H | H | H | EP-A 177 913 |
| 12.50 | n-C$_3$H$_7$ | CH$_2$-(thien-2-yl) | tetrahydrothiopyranyl | H | H | H | EP-A 177 913 |
| 12.51 | CH$_3$ | CH$_2$-(thien-2-yl) | tetrahydropyranyl | H | H | H | EP-A 177 913 |

TABLE 12-continued

Structure VI: cyclohexenone with OR^i, =NOR^e, R^d, R^f, R^g, R^h substituents

| No. | R^d | R^e | R^f | R^g | R^h | R^i | Reference |
|---|---|---|---|---|---|---|---|
| 12.52 | C₂H₅ | -CH₂-(2-thienyl) | tetrahydropyran-4-yl | H | H | H | EP-A 177 913 |

TABLE 13

Structure VI with R^e = —CH₂(CH₂)₂CH₂—phenyl(Radicals); R^g, R^h, R^i = H

| No. | R^d | R^f | Radicals on phenyl ring | Physical data [NMR* (δ in ppm)] |
|---|---|---|---|---|
| 13.01 | C₂H₅ | tetrahydropyran-4-yl (O) | 4-F | 2.9 (broad, 2H); 4.1 (broad, 2H) |
| 13.02 | n-C₃H₇ | tetrahydropyran-4-yl (O) | 4-F | 2.9 (t, 2H); 4.05 (broad, 2H) |
| 13.03 | C₂H₅ | tetrahydrothiopyran-4-yl (S) | 4-F | 2.9 (t, 2H); 4.05 (broad, 2H) |
| 13.04 | n-C₃H₇ | tetrahydrothiopyran-4-yl (S) | 4-F | 2.9 (t, 2H); 4.05 (broad, 2H) |
| 13.05 | C₂H₅ | tetrahydropyran-4-yl (O) | 4-F | 4.05 (broad, 2H) |
| 13.06 | n-C₃H₇ | tetrahydropyran-4-yl (O) | 4-F | 4.05 (broad, 2H) |
| 13.07 | C₂H₅ | tetrahydropyran-4-yl (O) | 4-Cl | 2.9 (t, 2H); 4.05 (broad, 2H) |
| 13.08 | n-C₃H₇ | tetrahydropyran-4-yl (O) | 4-Cl | 2.9 (t, 2H); 4.05 (broad, 2H) |

TABLE 13-continued

Structure VI: cyclohexenone with OH, =N-O-CH₂(CH₂)₂CH₂-phenyl (with radicals), R^f, R^d substituents, with R^e = —CH₂(CH₂)₂CH₂—(phenyl with Radicals); R^g, R^h, R^i = H

| No. | R^d | R^f | Radicals on phenyl ring | Physical data [NMR* (δ in ppm)] |
|---|---|---|---|---|
| 13.09 | C₂H₅ | tetrahydropyran (O) | 4-Cl | 2.9 (t, 2H); 4.05 (broad, 2H) |
| 13.10 | n-C₃H₇ | tetrahydropyran (O) | 4-Cl | 2.9 (broad, 2H); 4.05 (broad, 2H) |
| 13.11 | C₂H₅ | tetrahydrothiopyran (S) | 4-Cl | 4.05 (broad, 2H) |
| 13.12 | n-C₃H₇ | tetrahydrothiopyran (S) | 4-Cl | 4.05 (broad, 2H) |

*selected signals

Herbicidal active ingredients and antidote compounds can be applied together or separately, after emergence, to the leaves and shoots of the crops and of the undesirable grasses. The antidote agent is preferably applied simultaneously with the herbicidal active ingredient. Separate application is also possible, the antidote being applied first to the field, followed by the herbicidal active ingredient. The herbicidal active ingredient and antidote may be present as a spray, formulated together or separately in suspendable, emulsifiable or soluble form.

Antidote effects are also achieved by treating the seeds of the crops or the seedlings with the antidote prior to sowing or prior to planting out. The herbicidal active ingredient is then applied alone in the conventional manner.

In the case of seed treatment, in general from 0.1 to 10 g, preferably from 1 to 2 g, of active ingredient are required per kilogram of seed.

In the application of the antidote by means of seed swelling or in the treatment of seedlings, solutions which contain the antagonistic ingredient in a concentration of from 1 to 10,000 ppm, in particular from 100 to 10,000 ppm, are preferably used.

For herbicidal 2-(4-hetaryloxy)- or 2-(4-aryloxy)-phenoxyacetic acid derivatives V, different amounts of an antidote compound are preferred when the herbicide is used in different crops. The ratios can be varied within wide ranges. They are also dependent on the structure of 2-(4-hetaryloxy)- or 2-(4-aryloxy)-phenoxyacetic acid derivatives V and on the particular target crop. Suitable weight ratios of herbicidal active ingredients to antidote compound are from 1:10 to 1:0.01, preferably from 1:4 to 1:0.1 parts by weight.

For the same cyclohexenone derivative VI, different amounts of an antidote compound are required when the cyclohexenone derivative VI is used in different crops. The ratios in which a cyclohexenone derivative VI and a pyrido-fused 4-oxo-4H-benzopyran I or I' are used can be varied within wide ranges. They are dependent on the structure of the cyclohexenone derivative VI, and of the 4-oxo-4H-benzopyran I or I' and on the particular crop. Suitable weight ratios of herbicidal active ingredient to antidote compound are from 1:10 to 1:0.01, preferably from 1:4 to 1:0.25, parts by weight both for joint and for separate applications.

The agents according to the invention or, in the case of separate application, the herbicidal active ingredients or the antidote are applied, for example, in the form of directly sprayable solutions, powders, suspensions, including concentrated aqueous, oily or other suspensions, or dispersions, emulsions, oil dispersions, pastes, dusts, broadcasting agents or granules, by spraying, nebulizing, dusting, broadcasting or pouring. The application forms depend entirely on the intended uses.

For the preparation of directly sprayable solutions, emulsions, pastes and oil dispersions, mineral oil fractions having a medium to high boiling point, such as kerosene or diesel oil, as well as coal tar oils and oils of vegetable or animal origin, aliphatic, cyclic or aromatic hydrocarbons, eg. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, and strongly polar solvents, eg. dimethylformamide, dimethyl sulfoxide, N-methylpyrrolidone and water, are suitable.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or dissolved in an oil or solvent, can be homogenized in water by means of wetting agents, adherents, dispersants or emulsifiers. However, it is also possible to prepare concentrates which consist of herbicidal active ingredient and/or antidote, wetting agents, adherents, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol-, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusts can be prepared by mixing and milling the herbicidal active ingredient and/or the antidote together with a solid carrier.

Granules, for example coated, impregnated and homogeneous granules, can be prepared by binding the active ingredients to solid carriers. Examples of solid carriers are mineral earths, such as silica gel, silicas, silica gels, silicates, talc, kaolin, attaclay, limestone, chalk, talc, bole, loess, clay, dolomite, kieselguhr, calcium sulfate, magnesium sulfate, magnesium oxide, milled plastics, fertilizers, eg. ammonium sulfate, ammonium phosphate, ammonium nitrate and ureas, and vegetable products, such as grain flours, bark meal, wood meal and nutshell meal, cellulosic powders and other solid carriers.

The formulations contain from 0.01 to 95, preferably from 0.5 to 90,% by weight of herbicidal active ingredient and antidote. The application rates of herbicidal active ingredient are from 0.1 to 5 kg/ha active ingredient (a.i.)

In addition to the pyrido-fused 4-oxo-4H-benzopyran I or I' as an antidote and the herbicide selected from the group consisting of the 2-(4-hetaryloxy)- or 2-(4-aryloxy)-phenoxyacetic acids V or the cyclohexenones VI, the novel herbicides may contain further herbicidal or growth-regulating active ingredients having a different chemical structure, the antagonistic effect being retained.

PREPARATION EXAMPLES

Example 1

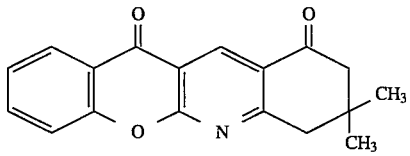

Active Ingredient Example 2.012

A mixture of 9.5 g (0.050 mol) of 2-amino-4-oxo-4H-chromene-3-carbaldehyde, 7.7 g (0.055 mol) of dimedone, 300 ml of ethanol and 5 ml of piperidine was refluxed for 5 hours. The precipitate which separated out on cooling was filtered off under suction, washed with ethanol and dried. Yield: 72%; mp. 250° C. (decomposition).

Example 2

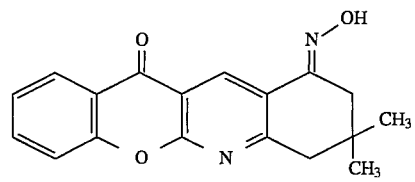

Active Ingredient Example 3.001

A mixture of 7.3 g (0.025 mol) of the product from Example 1, 3.5 g (0.050 mol) of hydroxylammonium chloride, 100 ml of ethanol, 20 ml of water and 2 ml of concentrated hydrochloric acid was refluxed for 5 hours. The precipitate obtained on cooling was filtered off under suction, washed with ethanol and dried. Yield: 91%; mp.>250° C.

Example 3

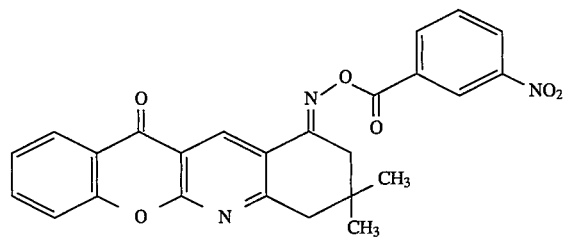

Active Ingredient Example 3.013

6.50 g (0.035 mol) of 3-nitrobenzoyl chloride were added, at room temperature, to a mixture of 9.27 g (0.030 mol) of the product from Example 2, 3.93 g (0.035 mol) of potassium tert-butylate and 70 ml of pyridine. Stirring was carried out for two hours, after which the suspension was added to 200 ml of 5% strength hydrochloric acid and the precipitate was filtered off under suction, washed with water and dried. Yield:: 90%, mp. 188°–190° C. (decomposition). Preparation of the starting materials according to J. Med. Chem. 28 (1985), 559.

Example 4

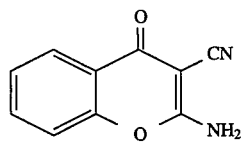

9.5 g (0.050 mol) of 2-amino-4-oxo-4H-chromene-3-carbaldehyde were heated to the boil with 3.8 g (0.055 mol) of hydroxylammonium chloride in 50 ml of formic acid for 45 minutes. 200 ml of water were added to the cooled solution, and the precipitate was filtered off under suction, washed with water and dried. Yield: 90%; mp.>250° C.

The intermediates or active ingredients shown in Tables 14 and 15 below can be prepared similarly to these Examples.

TABLE 14

Starting compounds

[Structure: R¹ₘ-substituted benzene fused with C(=O)-C(CHO)=C(NH₂)-O ring]

| Example no. | R¹ | mp. (°C.) | Reference |
|---|---|---|---|
| 14.001 | H | 250(Z) | 1) |
| 14.002 | 6-CH₃ | 282-4 | 1) |
| 14.003 | 6-C₂H₅ | 246-9(Z) | 1) |

TABLE 14-continued

Starting compounds

[Structure: R¹ₘ-substituted benzene fused with C(=O)-C(CHO)=C(NH₂)-O ring]

| Example no. | R¹ | mp. (°C.) | Reference |
|---|---|---|---|
| 14.004 | 7-OCH₃ | 251-4(Z) | 1) |

TABLE 15

Active ingredients I

[Structure: chromone-type with R¹ₘ on benzene ring (positions 3,4,5), carbonyl at position linking to pyridine with R⁷ and R⁶ substituents, N in pyridine]

| Example no. | R¹ | R⁶ | R⁷ | mp. (°C.) | Reference |
|---|---|---|---|---|---|
| 15.001 | H | C₆H₅ | C₆H₅ | | |
| 15.002 | 5-C₂H₅ | OH | CN | >300 | 1 |
| 15.003 | H | NH₂ | CN | >320 | 3 |
| 15.004 | H | NH₂ | COOC₂H₅ | 235-236 | 3 |
| 15.005 | H | OH | COOC₂H₅ | 239-242 | 3 |
| 15.006 | H | NH₂ | C₆H₅ | 248-250 | |
| 15.007 | H | CH₃ | CO—CH₃ | >250 | |
| 15.008 | H | CH₃ | C(CH₃)=N—OH | | |
| 15.009 | H | (cyclohexyl fused R⁶/R⁷) | | >250 | |
| 15.010 | H | (cyclohexanone fused R⁶/R⁷) | | 265 | |
| 15.011 | H | (4,4-dimethylcyclohexanone fused R⁶/R⁷) | | | |
| 15.012 | H | (o-methylbenzyl R⁶/R⁷) | | 250 | (decomposition) |
| 15.013 | H | | | | |
| 15.014 | H | (o-methylphenyl ketone R⁶/R⁷) | | >250 | |

TABLE 15-continued

Active ingredients I

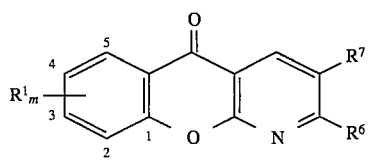

| Example no. | R¹ | R⁶ | R⁷ | mp. (°C.) | Reference |
|---|---|---|---|---|---|
| 15.015 | H | COOCH₃ | COOCH₃ | | |
| 15.016 | 3-OCH₃ | COOCH₃ | COOCH₃ | | |
| 15.017 | 3-OCH₃ | COOCH₃ | COOCH₃ | | |
| 15.018 | 4-i-C₃H₇ | COOCH₃ | COOCH₃ | | |
| 15.019 | 3-OCH₃ | COOH | COOH | | |
| 15.020 | H | CO—NH—C(CH₃)(i-C₃H₇)—CONH₂ | COOH | | |
| 15.021 | 4-i-C₃H₇ | CO—NH—C(CH₃)(i-C₃H₇)—CONH₂ | COOH | | |
| 15.022 | H | (N-substituted imidazolinone with CH₃ and i-C₃H₇) | COOH | | |
| 15.023 | 3-OCH₃ | (N-substituted imidazolinone with CH₃ and i-C₃H₇) | COOH | | |
| 15.024 | 4-i-C₃H₇ | (N-substituted imidazolinone with CH₃ and i-C₃H₇) | COOH | | |

TABLE 16

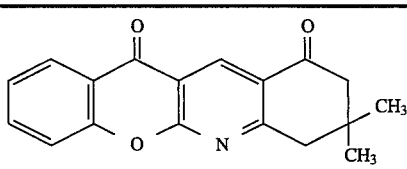

| Example no. | R | mp. (°C.) |
|---|---|---|
| 16.001 | =N—OH | >250 |
| 16.002 | =N—O—CO—CH₃ | 200 (Zers.) |
| 16.003 | =N—O—CO—CH₂—CH₃ | 166–172 |
| 16.004 | =N—O—CO—(CH₂)₂—CH₃ | 200 |
| 16.005 | =N—O—CO—(CH₂)₄—CH₃ | 182–186 |
| 16.006 | =N—O—CO—(CH₂)₁₄—CH₃ | 92–96 |
| 16.007 | =N—O—CO—C(CH₃)₃ | 210 (Zers.) |
| 16.008 | =N—O—CO—CH₂—C(CH₃)₃ | 186–190 |
| 16.009 | =N—O—CO—C₆H₅ | |
| 16.010 | =N—O—CO—(2-Cl—C₆H₄) | 180–190 |
| 16.011 | =N—O—CO—(2,4-Cl₂—C₆H₃) | >250 |
| 16.012 | =N—O—CO—(2-NO₂—C₆H₄) | |

TABLE 16-continued

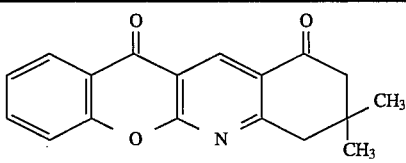

| Example no. | R | mp. (°C.) |
|---|---|---|
| 16.013 | =N—O—CO—(3-NO₂—C₆H₄) | 188–190 |
| 16.014 | =N—O—CO—(4-NO₂—C₆H₄) | >250 |

References
[1] A. Nohara et al., J. Med. Chem. 28 (1985) 559.
[2] G. P. Ellis et al., J. Chem. Soc. Perkin Trans I (1986), 1643.
[3] U. Petersen et al., Liebigs Ann. Chem. (1976), 1659.

Examples of the biological activity

The effect of various representatives of herbicides according to the invention or herbicide combinations, consisting of herbicide and antidote compound, on the growth of desired and undesirable plants in comparison with the herbicidal active ingredient alone is demonstrated by the following biological examples from greenhouse experiments:

The culture vessels used were plastic flower pots having a capacity of about 300 cm$^3$ and containing loamy sand with about 3.0% of humus as a substrate. The seeds of the test plants were sown shallowly and separately according to species and were moistened. Thereafter, the vessels were covered with transparent plastic covers until the seeds had germinated uniformly and the plants had started to grow.

For the postemergence treatment, the test plants were grown only to a height of growth of from 3 to 20 cm, depending on the form of growth, and only then treated. The herbicides were suspended or emulsified in water as a distributing agent and was sprayed by means of finely distributing nozzles.

The test vessels were placed in a greenhouse, 18°–30° C. being preferred for warmth-loving species and 10°–25° C. for those from temperate climates.

The test period extended over 3–5 weeks. During this time, the plants were tended and their reaction to the individual treatments was recorded.

The damage to the test plants was evaluated on the basis of a scale from 0 to 100% in comparison with untreated control plants. 0 means no damage and 100 means complete destruction of the plants.

The plants used in the greenhouse experiments consisted of the following species:

| Botanical name | Common name |
| --- | --- |
| Brachiaria platiphylla | broadleaf signalgrass |
| Setaria viridis | green foxtail |
| Triticum aestivum | winter wheat |
| Zea mays | Indian corn |

The following was used as an example herbicide of the cyclohexenone derivatives of the formula VI:

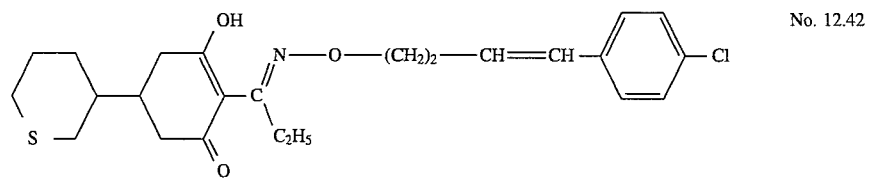

No. 12.42

The active ingredient 12.42 was applied as an emulsion concentrate containing 200 g of active ingredient/1 alone, with the addition of the amounts of solvents required for the antidotes, 80% by weight of cyclohexenone and 20% by weight of a surfactant (Emulphor EL*)) with 10% by weight of active ingredient.

For the postemergence treatment, all antidote compounds were formulated as a mixture consisting of 80% by weight of cyclohexenone and 20% by weight of surfactant (Emulphor EL*)) with 10% by weight of active ingredient.

Tables 17 to 19 below document the fact that the novel compounds having antidote activity substantially improve the toleration of the active ingredient 12.42 by crops which belong to the Gramineae family (grasses).

TABLE 17

Improvement of the toleration of the herbicidal active ingredient 12.42 by crops through combination with the compound 15.004 in postemergence application in the greenhouse

| Application rate [kg/ha a.i.] | | Test plants and damage [%] | | |
| --- | --- | --- | --- | --- |
| | | Crops | | |
| Herbicide 12.42 | Antidote 15.004 | Triticum aestivum[1] | Zea mays | Undesirable plant Setaria viridis |
| 0.25 | — | 98 | 90 | 100 |
| 0.25 | 0.5 | 15 | 30 | 98 |

[1] Star variety

TABLE 18

Improvement of the toleration of the herbicide 12.42 by corn through admixture with the antidote compound 15.018 or 15.021 in postemergence application in the greenhouse

| Application rate [kg/ha a.i.] | | | Test plants and damage [%] | | |
| --- | --- | --- | --- | --- | --- |
| | | | Crop | Undesirable plants | |
| Herbicide | Antidote | | Zea | Brachiaria | Setaria |
| 12.42 | 14.012 | 15.021 | mays[1] | platiphylla | viridis |
| 0.125 | — | — | 65 | 100 | 98 |
| 0.125 | 0.125 | — | 20 | 95 | 98 |
| 0.125 | — | 0.125 | 25 | 98 | 95 |

[1] Lixis variety

TABLE 19

Improvement of the toleration of the herbicide 12.42 by corn and wheat by admixing the antidote compound 15.015 in postemergence application in the greenhouse

| Application rate [kg/ha a.i.] | | Test plants and damage [%] | | |
| --- | --- | --- | --- | --- |
| | | Crops | | |
| Herbicide 12.42 | Antidote 15.015 | Triticum aestivum[2] | Zea mays[1] | Undesirable plant Setaria viridis |
| 0.125 | — | 90 | 98 | 98 |
| 0.125 | 0.125 | 10 | 10 | 95 |

[1] Lixis variety
[2] Star variety

We claim:

1. A herbicidal composition containing at least one pyrido-fused 4-oxo-4H-benzopyran of the formula I'

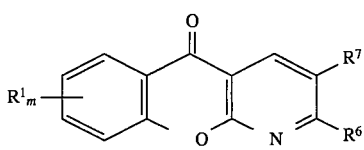

where m is 0, 1 or 2, and the radicals $R^1$ may be different when m is 2, $R^1$ is hydrogen, hydroxyl, halogen, nitro, $C_1$–$C_6$-alkyl, $C_1$–$C_6$-alkoxy, $C_1$–$C_6$-haloalkyl, $C_1$–$C_4$-haloalkoxy, $C_1$–$C_4$-alkylthio or a group $NR^2R^3$, $R^2$ is hydrogen or $C_1$–$C_4$-alkyl, $R^3$ is hydrogen, $C_1$–$C_4$-alkyl or a group —CO—$R^4$, —CS—$R^4$ or —$SO_2$—$R^5$, $R^4$ is $C_1$–$C_{20}$-alkyl, $C_1$–$C_6$-haloalkyl, $C_3$–$C_8$-cycloalkyl, $C_1$–$C_3$-aralkyl, amino, $C_1$–$C_4$-alkylamino, di-$C_1$–$C_4$-alkylamino, or phenyl or phenylamino where the aromatic ring may carry from one to three of the groups stated for $R^1$, $R^5$ is $C_1$–$C_4$-alkyl or is phenyl which may carry from one to three of the groups stated for $R^1$, $R^6$ is hydroxyl, $C_1$–$C_6$-alkoxy, $C_1$–$C_6$-alkyl or a group —NH—$R^8$ or —N($C_1$–$C_4$-alkyl)—$R^8$ where $R^8$ has one of the meanings of $R^3$, or $R^6$ is phenyl which may carry from one to three of the groups stated for $R^1$, or is $C_1$–$C_4$-alkyl-substituted 4-methyl-5-oxoimidazolin-2-yl or a group —CO—$R^9$ or —CS—$R^9$, $R^7$ is cyano or $C_1$–$C_6$-alkyl or is phenyl which may carry from one to three of the groups stated for $R^1$, or is a group —CH=N—$R^{10}$, —C($C_1$–$C_4$-alkyl)=N—$R^{10}$, —CO—$R^{11}$ or —CS—$R^{11}$, $R^9$ and $R^{11}$ are each $C_1$–$C_6$-alkyl, $C_1$–$C_6$-alkoxy, hydroxyl, amino or $C_1$–$C_4$-alkylamino or is branched $C_2$–$C_6$-alkyl which is substituted by an amido group $CONH_2$, or is di-$C_1$–$C_4$-alkylamino or aminophenyl where the aromatic ring may carry from one to three of the groups stated for $R^1$, $R^{10}$ is $C_1$–$C_4$-alkyl or $C_3$–$C_8$-cycloalkyl or is phenyl which may carry from one to three of the groups stated for $R^1$, or is hydroxyl, $C_1$–$C_8$-alkoxy or a group —O—CO—$R^{12}$ or —O—CS—$R^{12}$ where $R^{12}$ is $C_1$–$C_{20}$-alkyl, $C_1$–$C_6$-haloalkyl, $C_3$–$C_8$-cycloalkyl, phenyl-$C_1$–$C_3$-alkyl or phenyl where the phenyl rings may, if desired, furthermore carry from one to three of the radicals stated for $R^1$, or, if $R^6$ and $R^7$ are each alkyl or $R^6$ is alkyl and $R^7$ is a group —CO—H, —CO—($C_1$–$C_4$-alkyl), —CH=N—$R^{10}$ or —C($C_1$–$C_4$-alkyl)=N—$R^{10}$, $R^6$ and $R^7$ together form a 5-membered to 7-membered ring which is substituted by from one to four $C_1$–$C_4$-alkyl groups or is fused with a phenyl ring which may carry from one to three of the groups stated for $R^1$, and the agriculturally useful salts of the compounds I', where these compounds contain a basic nitrogen substituent or an acidic hydroxyl substituent, and at least one herbicidal active ingredient from the group consisting of B) the cyclohexenone oxime ether of the formula VI

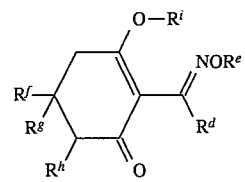

where $R^d$ is $C_1$–$C_4$-alkyl, $R^e$ is $C_1$–$C_4$-alkyl, $C_3$- or $C_4$-alkenyl, $C_3$- or $C_4$-alkynyl or partially or completely halogenated $C_3$- or $C_4$-alkenyl, a $C_1$–$C_4$-alkylene or $C_2$–$C_4$-alkenyl chain, both of which may furthermore carry from one to 3 $C_1$–$C_3$-alkyl radicals and/or halogen atoms, or a 3-membered to 6-membered alkylene chain or a 4-membered to 6-membered alkenylene chain which, if desired, is substituted by $C_1$–$C_3$-alkyl and each of which contains, as a chain member, an oxygen or sulfur atom which is not directly adjacent to the oxime ether moiety, all abovementioned chains carrying a terminal phenyl ring which in turn may be substituted by from one to three radicals selected from the group consisting of one benzyloxycarbonyl or phenyl radical and from one to three of each of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring additionally to carry a number of halogen atoms such that the total number of radicals is 4 or 5, or thienylmethyl which may furthermore carry a halogen atom, $R^f$ is $C_1$–$C_4$-alkyl which may be monosubstituted by $C_1$–$C_4$-alkylthio or $C_1$–$C_4$-alkoxy, a 5-membered or 6-membered saturated or monounsaturated ring system which, in addition to carbon members, may contain an oxygen or a sulfur atom or a sulfoxyl or sulfonyl group, where this ring may carry up to three of the following radicals: hydroxyl, halogen, $C_1$–$C_4$-alkyl, partially or completely halogenated $C_1$–$C_4$-alkyl, $C_1$–$C_4$-alkoxy and/or $C_1$–$C_4$-alkylthio, a 10-membered saturated or monounsaturated heterocyclic structure which contains two oxygen atoms or sulfur atoms and may be substituted by up to three $C_1$–$C_4$-alkyl groups and/or methoxy groups, phenyl, pyridyl, thiazolyl, pyrazolyl, pyrrolyl or isoxazolyl, where these groups may each carry from one to three radicals selected from the group consisting of $C_1$–$C_4$-alkyl, partially or completely halogenated $C_1$–$C_4$-alkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-alkylthio-$C_1$–$C_3$-alkyl, $C_1$–$C_4$-dialkoxy-$C_1$–$C_3$-alkyl, formyl, halogen and benzoylamino, $R^g$ is hydrogen or hydroxyl or, if $R^f$ is $C_1$–$C_6$-alkyl, $R_g$ is $C_1$–$C_6$-alkyl, $R^h$ is hydrogen, cyano, halogen, $C_1$–$C_4$-alkoxycarbonyl or $C_1$–$C_4$-alkylketoxime and $R^i$ is hydrogen or one equivalent of an agriculturally useful cation.

2. A herbicidal composition as claimed in claim 1, wherein the weight ratio of pyrido-fused 4-oxo-4H-benzopyran I' to herbicidal active ingredient B) is from 10:1 to 0.01:1.

3. A method for selectively controlling undesirable plant growth, wherein a pyrido-fused 4-oxo-4H-benzopyran of the formula I' as defined in claim 1 and B) a cyclohexenone derivative of the formula VI as defined in claim 4 are applied, simultaneously or in succession, before, during or after sowing of the crops or before or during emergence of the crops.

4. A method for preventing damage to crops by

B) cyclohexenone derivatives of the formula VI as defined in claim 1, wherein the seed of the corps is treated with an antagonistic amount of pyrido-fused 4-oxo-4H-benzopyran of the formula I' as defined in claim 1.

5. A method for selectively controlling undesirable plant growth, wherein the leaves of the crops and of the undesirable plants are treated by the postemergence method, simultaneously or in succession, with a pyrido-fused 4-oxo-4H-benzopyran of the formula I' as defined in claim 1 and with a cyclohexenone derivative of the formula VI as defined in claim 1.

6. A method as defined in claim 3, wherein the crops are barley, wheat, corn, millet or rice.

7. A method as defined in claim 4, wherein the crops are barley, wheat, corn, millet or rice.

8. A method as defined in claim 5, wherein the crops are barley, wheat, corn, millet or rice.

* * * * *

UNITED STATES PATENT AND TRADEMARK OFFICE
CERTIFICATE OF CORRECTION

PATENT NO. : 5,561,100

DATED : October 1, 1996

INVENTOR(S) : HAGEN et al.

It is certified that error appears in the above-indentified patent and that said Letters Patent is hereby corrected as shown below:

Column 56, claim 1, line 56, "$C_1 \propto C_6$-" should be -- $C_1$-$C_6$ --.

Signed and Sealed this

Eighteenth Day of February, 1997

Attest:

Attesting Officer

BRUCE LEHMAN

Commissioner of Patents and Trademarks